(12) United States Patent
Thomas et al.

(10) Patent No.: US 8,962,342 B2
(45) Date of Patent: Feb. 24, 2015

(54) NEAR-INFRARED DYES AS SURFACE ENHANCED RAMAN SCATTERING REPORTERS

(75) Inventors: Joseph Thomas, Raleigh, NC (US); Rajendra R. Bhat, Raleigh, NC (US); W. Shannon Dillmore, Raleigh, NC (US); Douglas B. Sherman, Durham, NC (US)

(73) Assignee: Beckton, Dickinson and Company, Franklin Lakes, NJ (US)

( * ) Notice: Subject to any disclaimer, the term of this patent is extended or adjusted under 35 U.S.C. 154(b) by 983 days.

(21) Appl. No.: 12/134,594

(22) Filed: Jun. 6, 2008

(65) Prior Publication Data

US 2008/0305489 A1  Dec. 11, 2008

Related U.S. Application Data

(60) Provisional application No. 60/942,329, filed on Jun. 6, 2007.

(51) Int. Cl.
| | |
|---|---|
| *G01N 21/65* | (2006.01) |
| *G01N 33/58* | (2006.01) |
| A61K 49/00 | (2006.01) |
| *B82Y 5/00* | (2011.01) |
| *B82Y 15/00* | (2011.01) |
| *B82Y 30/00* | (2011.01) |
| *C09B 23/10* | (2006.01) |
| *C09B 63/00* | (2006.01) |

(52) U.S. Cl.
CPC .......... *G01N 33/587* (2013.01); *A61K 49/0021* (2013.01); *A61K 49/0065* (2013.01); *A61K49/0093* (2013.01); *B82Y 5/00* (2013.01); *B82Y 15/00* (2013.01); *B82Y 30/00* (2013.01); *C09B 23/105* (2013.01); *C09B 63/00* (2013.01); *G01N 21/658* (2013.01)

USPC ............ 436/172; 436/173; 436/526; 436/546

(58) Field of Classification Search
CPC . G01N 33/533; G01N 33/582; G01N 33/586; G01N 21/658; A01B 43/80; A01B 43/82; C07D 285/01; C07D 285/12; A61K 49/0021; A61K 49/0065; A61K 49/0093; B82Y 15/00; B82Y 30/00
See application file for complete search history.

(56) References Cited

U.S. PATENT DOCUMENTS

| | | |
|---|---|---|
| 5,250,613 A | 10/1993 | Bergstrom et al. |
| 5,266,498 A | 11/1993 | Tarcha et al. |
| 5,270,193 A | 12/1993 | Eveleigh |
| 5,376,556 A | 12/1994 | Tarcha et al. |
| 5,472,881 A | 12/1995 | Beebe et al. |
| 5,567,628 A | 10/1996 | Tarcha et al. |
| 5,721,102 A | 2/1998 | Vo-Dinh |
| 6,344,272 B1 | 2/2002 | Oldenburg et al. |
| 6,514,767 B1 | 2/2003 | Natan |
| 6,685,986 B2 | 2/2004 | Oldenburg et al. |
| 6,699,724 B1 | 3/2004 | West et al. |
| 6,913,825 B2 | 7/2005 | Ostafin et al. |
| 7,002,679 B2 | 2/2006 | Brady et al. |
| 7,169,556 B2 | 1/2007 | Park et al. |
| 7,563,891 B2 * | 7/2009 | Pitner et al. ................... 544/105 |
| 7,588,827 B2 * | 9/2009 | Nie et al. ........................ 428/403 |
| 2003/0165942 A1 | 9/2003 | Czerney et al. |
| 2006/0030056 A1 | 2/2006 | Fort et al. |
| 2006/0046313 A1 | 3/2006 | Roth et al. |
| 2006/0054506 A1 | 3/2006 | Natan et al. |
| 2006/0078908 A1 | 4/2006 | Pitner et al. |
| 2006/0240572 A1 | 10/2006 | Carron et al. |
| 2006/0280652 A1 | 12/2006 | Pitner et al. |
| 2007/0165219 A1 | 7/2007 | Natan et al. |
| 2008/0044856 A1 | 2/2008 | Amiss et al. |

FOREIGN PATENT DOCUMENTS

| | | |
|---|---|---|
| EP | 0 874 242 A1 | 10/1998 |
| JP | 63304000 A | 12/1988 |
| JP | 2007502716 A | 2/2007 |
| JP | 2007514169 A | 5/2007 |
| WO | WO 99/17120 | 4/1999 |
| WO | WO 03/020966 | 3/2003 |
| WO | WO 03/053398 | 7/2003 |
| WO | WO 2005/010529 | 2/2005 |
| WO | WO 2005/040461 | 5/2005 |

| WO | WO 2005/069006 A1 | 7/2005 |
| WO | WO 2006/025887 A2 | 3/2006 |
| WO | WO 2006/036003 | 4/2006 |
| WO | WO 2007/018551 A2 | 2/2007 |
| WO | WO/2008/116093 A2 | 9/2008 |

OTHER PUBLICATIONS

Santra et al. Luminescent nanoparticle probes for bioimaging. J. Nanosci. Nanotech. 2004, vol. 4, No. 6, pp. 590-599.*
Allara, D. L., and Nuzzo, R. G., Spontaneously Organized Molecular Assemblies. 1. Formation, Dynamics, and Physical Properties of n-Alkanoic Acids Adsorbed from Solution on an Oxidized Aluminum Surface, Langmuir, 1985, p. 45, vol. 1.
Averitt, R. D., et al., Ultrafast optical properties of gold nanoshells, JOSA B, 1999, pp. 1824-1832, vol. 16, No. 10.
Breuzard, G., et al., Surface-enhanced Raman scattering reveals adsorption of mitoxantrone on plasma membrane of living cells, Biochem. Biophys. Res. Comm , 2004, pp. 615-621, vol. 320.
Brillhart, K.L., and Ngo, T.T., Use of Microwell Plates Carrying Hydrazide Groups to Enhance Antibody Immobilization in Enzyme Immunoassays, J. Immunol. Methods, 1991, pp. 19-25, vol. 144, No. 1.
Cao, Y.W., et al., DNA-modified core-shell Ag/Au nanoparticles, J. Am. Chem. Soc., 2001, pp. 7961-7962, vol. 123, No. 32.
Chen, H., et al , Immobilization of Heparin on a Silicone Surface Through a Heterobifunctional PEG Spacer, Biomaterials, 2005, pp. 7418-7424, vol. 26.
Cui, Y., et al., Multianalyte Immunoassay Based on Surface-Enhanced Raman Spectroscopy, Journal of Raman Spectroscopy, 2007, pp. 896-902, vol. 38, No. 7.
Dubertret, B., et al., In Vivo Imaging of Quantum Dots Encapsulated in Phospholipid Micelles, Science, 2002, pp. 1759-1762, vol. 298.
Eltekova, N.A. and Eltekov, Y.A., Adsorption of Aromatic Compounds from Solutions on Titanium Dioxide and Silica, Langmuir, 1987, pp. 951-957, vol. 3.
Emory, S. R., and Nie, S., Near-field surface-enhanced Raman spectroscopy on single silver nanoparticles, Anal. Chem., 1997, p. 2631, vol. 69.
Fleishman, M., et al., Raman spectra of pyridine adsorbed at a silver electrode, Chem. Phys. Lett., 1974, p. 163, vol. 26.
Gong, J.-L., $Ag/SiO_2$ Core-Shell Nanoparticle-Based Surface-Enhanced Raman Probes for Immunoassay of Cancer Marker Using Silica-Coated Magnetic Nanoparticles as Separation Tools, Biosensors and Bioelectronics, 2007, pp. 1501-1507, vol. 22.
Grabar, K.C., et al., Preparation and Characterization of Au Colloid Monolayers, Anal. Chem., 1995, pp. 735-743, vol. 67.
Hickman, J.J., et al., J. Am. Chem. Soc., 1989, p. 7271, vol. 111.
Hirsch, L.R., et al., A Whole Blood Immunoassay Using Gold Nanoshells, Anal. Chem., 2003, pp. 2377-2381, vol. 75, No. 10.
Hoffman, W. L. and O'Shannessy, D. J., Site Specific Immobilization of Antibodies by Their Oligosaccharide Moieties to New Hydrazide Derivatized Solid Supports, J. Immunol. Method, 1988, pp. 113-120, vol. 112.
Hubbard, A. T., Electrochemistry of Well-Defined Surfaces, Acc. Chem. Res., 1980, pp. 177-184, vol. 13.
Jackson, J.B., et al., Surface-Enhanced Raman Scattering on Tunable Plasmonic Nanoparticle Substrates, Proc. Natl. Acad. Sci. U.S.A., 2004, pp. 17930-14935, vol. 101, No. 52.
Jeanmaire, D. L., and Van Dyne, R. P., Surface Raman spectroelectrochemistry. 1. Heterocyclic, aromatic, and aliphatic-amines absorbed on anodized silver electrode. J. Electroanal. Chem., 1977, pp. 1-20, vol. 84, No. 1.
Kneipp, K. et al., Single molecule detection using surface-enhanced Raman scattering (SERS), Phys. Rev. Lett., 1997, pp. 1667-1670, vol. 78, No. 9.
Kneipp, K., et al., Surface-enhanced Raman spectroscopy in single living cells using gold nanoparticles, Appl. Spectrosc., 2002, pp. 150-154, vol. 56, No. 2.
Lee, H. et al., Adsorption of Ordered Zirconium Phosphonate Multilayer Films on Silicon and Gold Surfaces, J. Phys. Chem., 1988, pp. 2597-2601, vol. 92.
Looger, L. L., et al., Computational Design of Receptor and Sensor Proteins With Novel Functions, Nature, 2003, pp. 185-190, vol. 423, No. 6936.
Maoz, R., and Sagiv, J., Penetration-Controlled Reactions in Organized Monolayer Assemblies. 1. Aqueous Permanganate Interaction with Monolayer and Multilayer Films of Long-Chain Surfactants, Langmuir, 1987, pp. 1034-1044, vol. 3.
Maoz, R., and Sagiv, J., Penetration-Controlled Reactions in Organized Monolayer Assemblies. 2. Aqueous Permanganate Interaction with Monolayer and Multilayer Films of Long-Chain Surfactants, Langmuir, 1987, pp. 1045-1051, vol. 3.
Morjani, H., et al., Molecular and cellular interactions between intoplicine, DNA, and topoisomerase II studied by surface-enhanced Raman scattering spectroscopy, Cancer Res., 1993, pp. 4784-4790, vol. 53.
Mucic, R.C., et al., Synthesis and Characterization of DNA with Ferrocenyl Groups Attached to their 5'-termini: Electrochemical Characterization of a Redox-active Nucleotide Monolayer, Chem. Commun., 1996, pp. 555-557.
Mucic, R.C., et al., DNA-directed synthesis of binary nanoparticle network materials, J. Am. Chem. Soc., 1998, pp. 12674, vol. 120, No. 48.
Mulvaney, S. P., et al., Glass-Coated, Analyte-Tagged Nanoparticles: A New Tagging System Based on Detection with Surface-Enhanced Raman Scattering, Langmuir, 2003, pp. 4784-4790, vol. 19, No. 11.
Nabiev, I. R., et al., Selective analysis of antitumor drug interactions with living cancer cells as probed by surface-enhanced Raman spectroscopy, Eur. Biophys. J., 1991, pp. 311-316, vol. 19.
Natan, M., Going for the Gold: Multiplexed Optical Detection Tags Based on SERS-Active Gold Nanoparticles, Nanotech Briefs, Feb. 2007, vol. 4, No. 2.
Ni, J., et al., Immunoassay Readout Method Using Extrinsic Raman Labels Adsorbed on Immunogold Colloids, Anal. Chem., 1999, p. 4903, vol. 71.
Nicewarner-Pena, S. R., et al., Submicrometer metallic barcodes, Science, 2001, pp. 137-141, vol. 294.
Nie, S., and Emory, S. R., Probing single molecules and single nanoparticles by surface-enhanced Raman scattering, Science, 1997, pp. 1102-1106, vol. 275.
Nuzzo, R. G., et al., Spontaneously Organized Molecular Assemblies. 3. Preparation and Properties of Solution Adsorbed Monolayers of Organic Disulfides on Gold Surfaces, J. Am. Chem. Soc., 1987, pp. 2358-2368, vol. 109.
O'Shannessy, D. J. and Hoffman, W. L., Site-Directed Immobilization of Glycoproteins on Hydrazide-Containing Solid Supports, Biotechnol. Appl. Biochem. 1987, pp. 488-496, vol. 9.
O'Shannessy, D. J., Hydrazido-derivatized Supports in Affinity Chromatography, J. Chromatograph., 1990, pp. 13-21, vol. 510.
Polancyzk, C. A., et al., Cardiac troponin I as a predictor of major cardiac events in emergency department patients with acute chest pain, J. Am. Coll. Cardiol., 1998, pp. 8-14, vol. 32.
Qian, X.-M., et al., A New Class of Nontoxic Nanoparticle Tags Based on Surface Enhanced Raman Scattering, Colloidal Quantum Dots for Biomedical Applications II, Osinski, M., Jovin, T. M., and Yamamoto, K., eds., Proc. of SPIE, 2007, p. 64480O-1, vol. 6448.
Rohr, T. E., et al., Immunoassay employing surface-enhanced Raman spectroscopy, Anal. Biochem., 1989, p. 388, vol. 182.
Smith, E. R. and Storch, J., The Adipocyte Fatty Acid-Binding Protein Binds to Membranes by Electrostatic Interactions, J. Biol. Chem., 1999, pp. 35325-35330, vol. 274, No. 50.
Soriaga, M. P. and Hubbard, A. T., Determination of the Orientation of Aromatic Molecules Adsorbed on Platinum Electrodes. The Effect of Solute Concentration, J. Am. Chem. Soc., 1982, pp. 3937-3945, vol. 104.
Talley, C.E., et al., Nanoparticle Based Surface-Enhanced Raman Spectroscopy, Nato Advanced Study Institute: Biophotonics, Jan. 6, 2005, Ottawa, Canada.
Timmons, C. O. and Zisman, W. A., Investigation of Fatty Acid Monolayers on Metals by Contact Potential Measurements, J. Phys. Chem., 1965, pp. 984-990, vol. 69.

Tkachenko, A. G., et al., Cellular trajectories of peptide-modified gold particle complexes: comparison of nuclear localization signals and peptide transduction domains, Bioconjugate Chem., 2004, pp. 482-490, vol. 15.
Tuchin, V. V., Handbook of optical biomedical diagnostics, 2002, Bellingham, Wash., USA: SPIE Press.
Unsworth, L. D., et al., Protein Resistance of Surfaces Prepared by Sorption of End-Thiolated Poly(ethylene glycol) to Gold: Effect of Surface Chain Density, Langmuir, 2005, pp. 1036-1041, vol. 21, No. 3.
Wasserman, S.R., et al., Structure and Reactivity of Alkylsiloxane Monolayers Formed by Reaction of Alkyltrichlorosilanes on Silicon Substrates, Langmuir, 1989, pp. 1074-1087, vol. 5.
Whitesides, G.M., Proceedings of the Robert A. Welch Foundation 39th Conference on Chemical Research Nanophase Chemistry, 1996, pp. 109-121, Houston, Tex.
Xu, S., Surface-Enhanced Raman Scattering Studies on Immunoassay, J. Biomedical Optics, 2005, p. 031112, vol. 10, No. 3.
Zalipsky, S., Functionalized Poly(ethylene glycol) for Preparation of Biologically Relevant Conjugates, Bioconjugate Chem., 1995, pp. 150-165, vol. 6.
Doering, W.E., and Nie, S., "Spectroscopic Tags Using Dye-Embedded Nanoparticles and Surface-Enhanced Raman Scattering," *Anal. Chem.*, 2003, pp. 6171-6176, vol. 75(22).
Le Bris, M.T., "Synthesis and Properties of Some 7-Dimethylamino-1,4-Benzoxazin-2-Ones," *J. Heterocyclic Chem.*, 1985, pp. 1275-1280, vol. 22.
Schiedel, M.S., et al., "Single-Compound Libraries of Organic Materials: Parallel synthesis and Screening of Fluorescent Dyes," *Agnew. Chem. Int. Ed.*, 2001, pp. 4677-4680, vol. 40(24).
Database Beilstein, Beilstein Institute for Organic Chemistry, Frankfurt-Main, DE, Citation No. 5586635, 1990, XP-002495465; Abstract.
Database Beilstein, Beilstein Institute for Organic Chemistry, Frankfurt-Main, DE, Citation No. 5599570, 1991, XP-002495464; Abstract.
Database Beilstein, Beilstein Institute for Organic Chemistry, Frankfurt-Main, DE, Citation No. 5810873, 1992, XP-002495463; Abstract.

* cited by examiner

*Primary Examiner* — Shafiqul Haq
(74) *Attorney, Agent, or Firm* — Lerner, David, Littenberg, Krumholz & Mentlik, LLP

(57) ABSTRACT

Nanoparticles comprising surface-enhanced Raman scattering (SERS) reporter molecules of the formula A-Y and methods of their use are disclosed, wherein A is selected from the group consisting of:

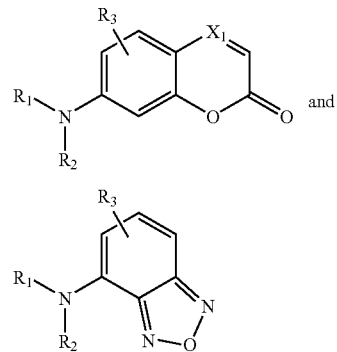

wherein $X_1$ is $CR_4$ or N; and Y is selected from the group consisting of:

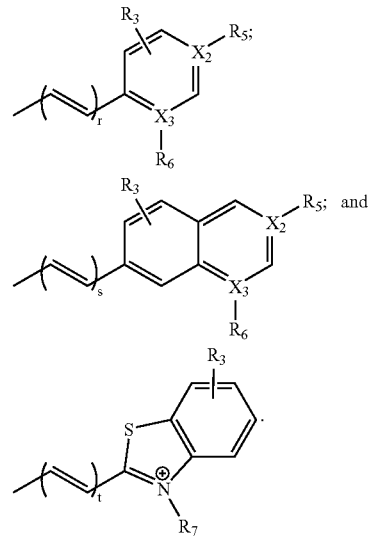

18 Claims, 8 Drawing Sheets

NEAR-INFRARED DYES AS SURFACE ENHANCED RAMAN SCATTERING REPORTERS

CROSS REFERENCE TO RELATED APPLICATION

This application claims the benefit of U.S. Provisional Application No. 60/942,329, filed on Jun. 6, 2007, which is herein incorporated by reference in its entirety.

TECHNICAL FIELD

The presently disclosed subject matter relates to near-infrared dyes and their use as surface-enhanced Raman scattering (SERS) reporter molecules.

BACKGROUND

When a molecule is irradiated with photons of a particular frequency, the photons are scattered. The majority of the incident photons are elastically scattered without a change in frequency (Rayleigh scattering), whereas a small fraction of the incident photons (approximately 1 in every $10^8$) interact with a vibrational mode of the irradiated molecule and are inelastically scattered. The inelastically scattered photons are shifted in frequency and have either a higher frequency (anti-Stokes) or a lower frequency (Stokes). By plotting the frequency of the inelastically scattered photons against their intensity, a unique Raman spectrum of the molecule is observed. The low sensitivity of conventional Raman spectroscopy, however, has limited its use for characterizing biological samples in which the target analyte(s) typically are present in small quantities.

When a Raman-active molecule is adsorbed on or in close proximity to, e.g., within about 50 Å of, a metal surface, the intensity of a Raman signal arising from the Raman-active molecule can be enhanced. This enhancement is referred to as the surface-enhanced Raman scattering (SERS) effect. The SERS effect was first reported in 1974 by Fleishman et al., who observed intense Raman scattering from pyridine adsorbed on a roughened silver electrode surface. See Fleishman et al., "Raman spectra of pyridine adsorbed at a silver electrode," *Chem. Phys. Lett.*, 26, 163 (1974); see also Jeanmaire, D. L., and Van Dyne, R. P., "Surface Raman spectroelectrochemistry. 1. Heterocyclic, aromatic, and aliphatic-amines absorbed on anodized silver electrode." *J. Electroanal. Chem.*, 84(1), 1-20 (1977); Albrecht, M. G., and Creighton, J. A., "Anomalously intense Raman spectra of pyridine at a silver electrode," *J. A. C. S.*, 99, 5215-5217 (1977). Since then, SERS has been observed for a number of different molecules adsorbed on the surface of metal surfaces. See, e.g., A. Campion, A. and Kambhampati, P., "Surface-enhanced Raman scattering," *Chem. Soc. Rev.*, 27, 241 (1998).

The magnitude of the SERS enhancement depends on a number of parameters, including the position and orientation of various bonds present in the adsorbed molecule with respect to the electromagnetic field at the metal surface. The mechanism by which SERS occurs is thought to result from a combination of (i) surface plasmon resonances in the metal that enhance the local intensity of the incident light; and (ii) formation and subsequent transitions of charge-transfer complexes between the metal surface and the Raman-active molecule.

The SERS effect can be observed with Raman-active molecules adsorbed on or in close proximity to metal colloidal particles, metal films on dielectric substrates, and metal particle arrays, including metal nanoparticles. For example, Kneipp et al. reported the detection of single molecules of a dye, cresyl violet, adsorbed on aggregated clusters of colloidal silver nanoparticles. See Kneipp, K. et al., "Single molecule detection using surface-enhanced Raman scattering (SERS), *Phys. Rev. Lett.*, 78(9), 1667-1670 (1997). That same year, Nie and Emory observed the surfaced enhanced resonance Raman spectroscopy (SERRS) signal, wherein the resonance between the absorption energy of the Raman-active molecule and that of the nanoparticle yield an enhancement as large as about $10^{10}$ to about $10^{12}$, of a dye molecule adsorbed on a single silver nanoparticle, where the nanoparticles ranged from spherical to rod-like and had a dimension of about 100 nm. See Nie, S., and Emory, S. R., "Probing single molecules and single nanoparticles by surface-enhanced Raman scattering," *Science*, 275, 1102-1106 (1997); Emory, S. R., and Nie, S., "Near-field surface-enhanced Raman spectroscopy on single silver nanoparticles," *Anal. Chem.*, 69, 2631 (1997).

Even with the enhanced signal due to the SERS or SERRS effect, the use of Raman spectroscopy can be limited in diagnostic assays and applications requiring a high sensitivity. Accordingly, there is a need in the art for SERS-active reporter molecules that give rise to an increased Raman signal when compared to SERS-active reporter molecules known in the art. The presently disclosed subject matter addresses, in whole or in part, these and other needs in the art.

BRIEF SUMMARY

In some embodiments, the presently disclosed subject matter provides a nanoparticle comprising a surface enhanced Raman scattering (SERS)-active reporter molecule of the formula:

A-Y wherein:
A is selected from the group consisting of:

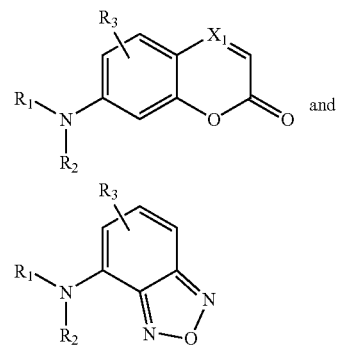

wherein $X_1$ is $CR_4$ or N;
Y is selected from the group consisting of:

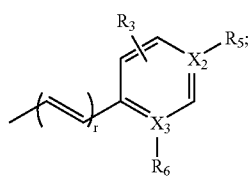

-continued

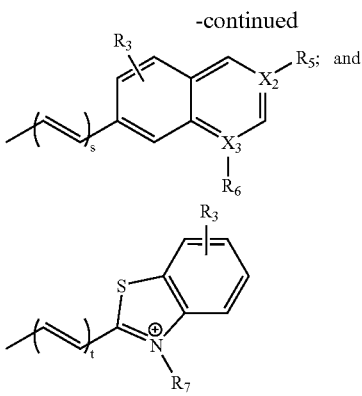

wherein:

r, s, and t are each independently an integer from 1 to 8;

each $X_2$ and $X_3$ is independently selected from the group consisting of C, S, and N, under the proviso that (i) when $X_2$ is C or S, $R_5$ is Z, or when $X_3$ is C or S, $R_6$ is Z, as Z is defined herein below; (ii) if both $X_2$ and $X_3$ are N at the same time, at least one of $R_5$ and $R_6$ is absent; and (iii) when $X_2$ is N, $R_5$ when present is Z', or when $X_3$ is N, $R_6$ when present is Z', wherein Z' is selected from the group consisting of:

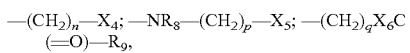

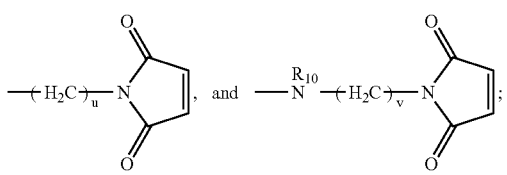

wherein:

n, p, q, u, and v are each independently an integer from 1 to 8;

$X_4$ and $X_5$ are each independently selected from the group consisting of hydroxyl, amino, and thiol;

$X_6$ is O or $NR_{11}$;

wherein:

each $R_1$, $R_2$, $R_3$, $R_4$, $R_5$, $R_6$, $R_8$, $R_{10}$, $R_{11}$, and Z is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;

$R_7$ is Z';

$R_9$ is $—(CH_2)_m—X_7$ or $—(CH_2)_m—B$, wherein m is an integer from 1 to 8;

$X_7$ is halogen; and

B is a binding member having a binding affinity for a ligand or analyte to be detected.

In some embodiments, the presently disclosed subject matter provides a method for labeling a molecule, cell, bead, or solid support, the method comprising: (a) providing at least one of a molecule, cell, bead, or solid support; and (b) attaching a particle to the at least one of a molecule, cell, bead, or solid support, wherein the particle comprises a surface-enhanced Raman spectroscopy (SERS)-active nanoparticle having associated therewith a dye of Formula A-Y.

In some embodiments, the presently disclosed subject matter provides a method for detecting the presence or amount of one or more analytes in a biological sample, the method comprising: (a) providing a biological sample suspected of containing one or more analytes; (b) contacting the biological sample with a reagent comprising one or more SERS-active nanoparticles having associated therewith at least one specific binding member having an affinity for the one or more analytes and at least one SERS-active reporter molecule of Formula A-Y; (c) illuminating the biological sample with incident radiation at a wavelength to induce the SERS-active reporter molecule to produce a SERS signal; and (d) measuring the SERS signal to detect the presence or amount of one or more analytes in the biological sample.

In some embodiments, the presently disclosed subject matter provides a method for detecting the presence of one or more target structures in a sample cell, the method comprising: (a) contacting one or more sample cells with one or more SERS-active nanoparticles labeled with one or more binding members under conditions suitable for binding of the one or more binding members to one or more target structures in the sample cell, wherein the SERS-active nanoparticle has associated therewith a dye of Formula A-Y capable of producing a distinguishable Raman signal; and (b) detecting one or more distinguishable SERS signals from the sample cell to indicate the presence of the one or more target structures in the sample cell.

In some embodiments, the presently disclosed subject matter provides a kit including a reagent comprising one or more surface-enhanced Raman spectroscopy (SERS)-active nanoparticles having associated therewith at least one SERS-active reporter molecule of Formula A-Y.

Thus, it is an object of the presently disclosed subject matter to provide a nanoparticle comprising a SERS-active reporter molecule of Formula A-Y. It is another object of the presently disclosed subject matter to provide a method for labeling a molecule, cell, bead, or solid support, with a nanoparticle comprising a SERS-active reporter molecule of Formula A-Y. It is yet another object of the presently disclosed subject matter to provide a method for detecting the presence or amount of one or more analytes in a biological sample. It is another object of the presently disclosed subject matter to provide a method for detecting the presence of one or more target structures in a sample cell. It is another object of the presently disclosed subject matter to provide a kit including a reagent comprising one or more surface-enhanced Raman spectroscopy (SERS)-active nanoparticles having associated therewith at least one SERS-active reporter molecule of Formula A-Y.

Certain objects of the presently disclosed subject matter having been stated hereinabove, which are addressed in whole or in part by the presently disclosed subject matter, other objects will become evident as the description proceeds when taken in connection with the accompanying Examples and Drawings as best described herein below.

BRIEF DESCRIPTION OF THE DRAWING(S)

Having thus described the presently disclosed subject matter in general terms, reference will now be made to the accompanying drawings, which are not necessarily drawn to scale, and wherein:

FIG. 1 shows a Raman spectrum obtained from a Raman reporter molecule known in the art, e.g., trans-1,2-bis(4-pyridyl)ethylene (BPE) (dotted line) and a Raman spectrum of a presently disclosed near-infrared dye, e.g., coumarin picolinium (CoPic);

FIG. 2 shows a comparison of the Raman intensity observed with non-fluorescent Raman molecules and commercial dyes adsorbed on 60-nm spherical gold nanoparticles. FIG. 2A shows the Raman intensity of non-fluorescent Raman molecules adsorbed on 60-nm gold nanoparticles. FIG. 2B shows the Raman intensity of commercial dyes adsorbed on 60-nm spherical gold nanoparticles;

Figure 6A:
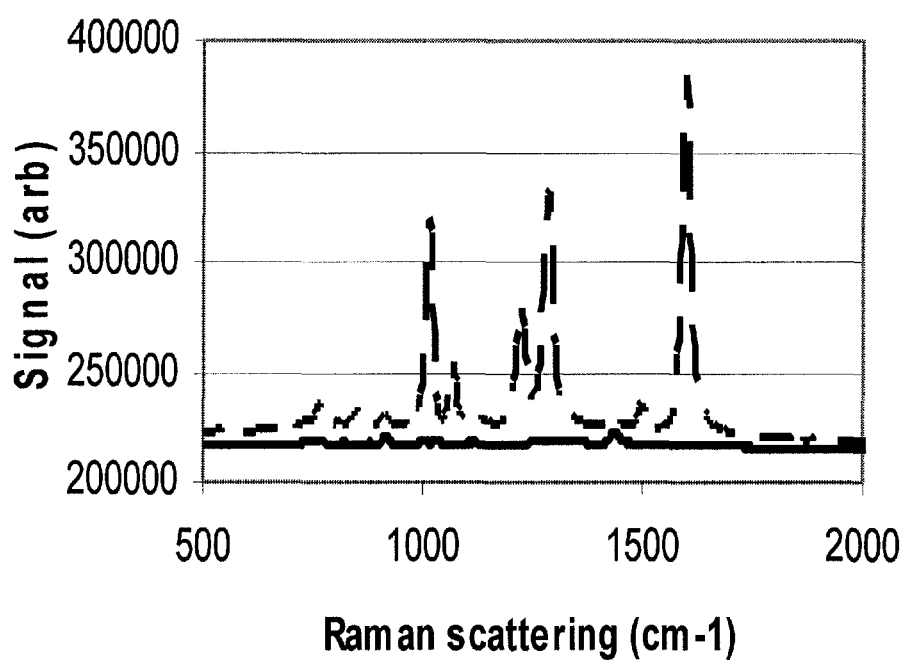
FIGS. 6A-6C show representative SERS spectra from the presently disclosed magnetic capture assays.
Figure 6B:
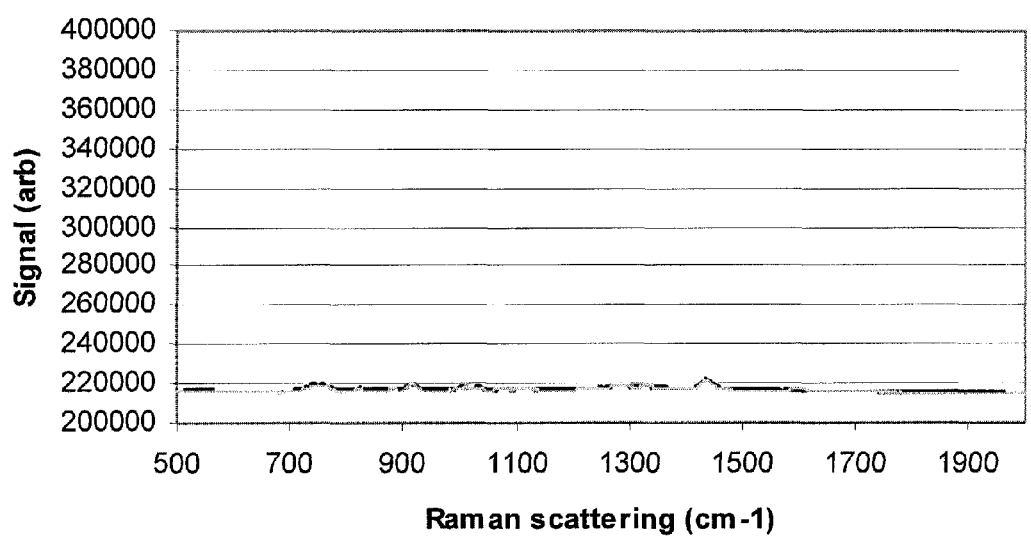
Figure 6C:
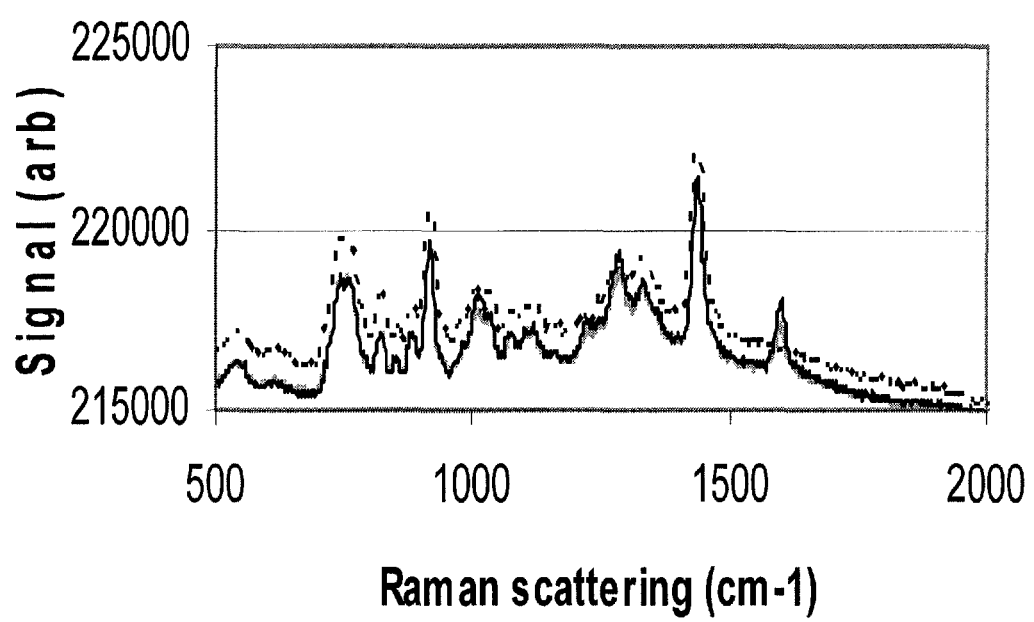

FIG. 6A shows the SERS spectra of an empty sample tube (solid line) and of oligonucleotide-coated SERS-active nanoparticles associated with oligonucleotide-coated magnetic particles (dashed line) in the absence of target DNA, wherein the oligonucleotide has been attached directly to the SERS-active nanoparticles and the magnetic particles, respectively, through biotin-streptavidin associations; and FIGS. 6B and 6C show representative SERS spectra of oligonucleotide-coated SERS-active nanoparticles associated with oligonucleotide-coated magnetic particles in the absence of target DNA, wherein the oligonucleotides have been attached to the SERS-active nanoparticles and the magnetic particles, respectively, via a polyethylene glycol linker molecule. FIG. 6C presents the same data as FIG. 6B on a more narrow scale. The dashed line in FIG. 6C represents the SERS spectrum of an empty sample tube and the solid lines represent the assay signal.

DETAILED DESCRIPTION

The presently disclosed subject matter now will be described more fully hereinafter with reference to the accompanying Drawings, in which some, but not all embodiments of the presently disclosed subject matter are shown. Many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

I. Nanoparticles Comprising Near-IR SERS-Active Reporter Molecules

The presently disclosed subject matter provides near-infrared dyes and their use as SERS-active reporter molecules, also referred to herein as SERS-active molecules, SERS-active dyes, or SERS-active labels. A "reporter molecule" refers to any molecule or chemical compound that is capable of producing a Raman spectrum when it is illuminated with radiation of a proper wavelength. A "reporter molecule" also can be referred herein as a "label," a "dye," a "Raman-active molecule," or "SERS-active molecule," each of which can be used interchangeably.

As described in more detail herein below, the intensity of the SERS signal observed for the presently disclosed SERS-active dyes when associated with, i.e., adsorbed on or attached to, a nanoparticle is higher than that observed for SERS-active reporter molecules and commercial dyes known in the art. The enhanced SERS signals observed for the presently disclosed SERS-active dyes allow for their use in applications, such as diagnostic assays using Raman spectroscopy as a detection method, optical imaging of tissues and cells, and other applications, where high sensitivity is required.

When used in a diagnostic assay, the enhanced SERS signals observed for the presently disclosed SERS-active dyes enable detection of biomarkers, including, but not limited to, proteins, nucleic acids, and metabolites, at lower concentrations than those measurable using SERS-active reporter molecules known in the art. This higher sensitivity is beneficial in applications where the Raman signal has to pass through, i.e., is transmitted through, a complex medium, such as whole blood or serum. Further, diagnostic assays with a higher sensitivity for analytes of interest can be required for early detection of a condition or a disease state in a subject.

A. Nanoparticles Comprising Near-IR SERS-Active Reporter Molecules of Formula A-Y In some embodiments, the presently disclosed subject matter provides a nanoparticle comprising a SERS-active reporter molecule of the Formula:

A-Y wherein:

A is selected from the group consisting of:

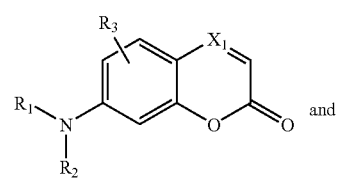

and

-continued

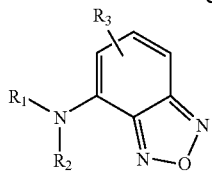

wherein $X_1$ is $CR_4$ or N;
Y is selected from the group consisting of:

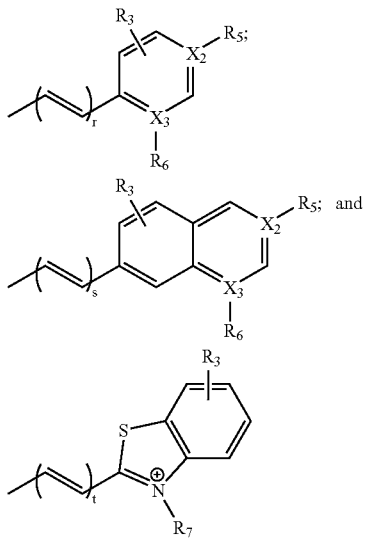

wherein:
r, s, and t are each independently an integer from 1 to 8;
each $X_2$ and $X_3$ is independently selected from the group consisting of C, S, and N, under the proviso that (i) when $X_2$ is C or S, $R_5$ is Z, or when $X_3$ is C or S, $R_6$ is Z, as Z is defined herein below; (ii) if both $X_2$ and $X_3$ are N at the same time, at least one of $R_5$ and $R_6$ is absent; and (iii) when $X_2$ is N, $R_5$ when present is Z', or when $X_3$ is N, $R_6$ when present is Z', wherein Z' is selected from the group consisting of:

—$(CH_2)_n$—$X_4$; —$NR_8$—$(CH_2)_p$—$X_5$; —$(CH_2)_q X_6 C(=O)$—$R_9$,

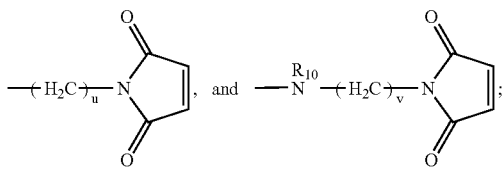

wherein:
n, p, q, u, and v are each independently an integer from 1 to 8;
$X_4$ and $X_5$ are each independently selected from the group consisting of hydroxyl, amino, and thiol;
$X_6$ is O or $NR_{11}$;
wherein:
each $R_1$, $R_2$, $R_3$, $R_4$, $R_5$, $R_6$, $R_8$, $R_{10}$, $R_{11}$, and Z is independently selected from the group consisting of H, alkyl, substituted alkyl, heteroalkyl, substituted heteroalkyl, cycloalkyl, substituted cycloalkyl, cyclo-heteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;

$R_7$ is Z';
$R_9$ is —$(CH_2)_m$—$X_7$ or —$(CH_2)_m$—B, wherein
m is an integer from 1 to 8;
$X_7$ is halogen; and
B is a binding member having a binding affinity for a ligand or analyte to be detected.

In some embodiments, the variable "A" of formula A-Y comprises a coumarin nucleus, an aza-coumarin nucleus, a benzoxadiazole nucleus, or analogs or derivatives thereof. Representative structures of a coumarin nucleus, an aza-coumarin nucleus, and a benzoxadiazole nucleus are provided immediately herein below:

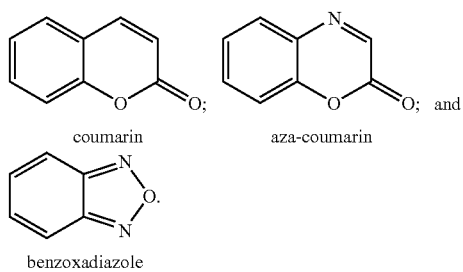

coumarin    aza-coumarin benzoxadiazole

As used herein, an "analog" refers to a chemical compound in which one or more individual atoms or functional groups of a parent compound have been replaced, either with a different atom or with a different functional group. For example, thiophene is an analog of furan, in which the oxygen atom of the five-membered furanyl ring is replaced by a sulfur atom.

As used herein, a "derivative" refers to a chemical compound that is derived from or obtained from a parent compound and contains essential elements of the parent compound, but typically has one or more different functional groups. Such functional groups can be added to a parent compound, for example, to improve the molecule's solubility, absorption, biological half life, Raman activity, and the like, or to decrease the toxicity of the molecule, eliminate or attenuate any undesirable side effect of the molecule, and the like. A derivative of a parent compound is meant to include any chemical modification, addition, deletion, or substitution to the parent compound. In some embodiments, a derivative of a parent compound can include any reaction product of the derivative, for example, the reaction product of the derivative with an amino acid residue. Accordingly, in some embodiments, the presently disclosed SERS-active nanoparticle can include a dye of Formula A-Y, wherein the dye nucleus includes a reactive group that can be conjugated, e.g., covalently attached, to an amino acid, for example, an amino acid residue of a protein. A non-limiting example of a derivative is an ester or amide of a parent compound having a carboxylic acid functional group.

In some embodiments, the SERS-active reporter dye molecule of Formula A-Y is selected from the group consisting of:

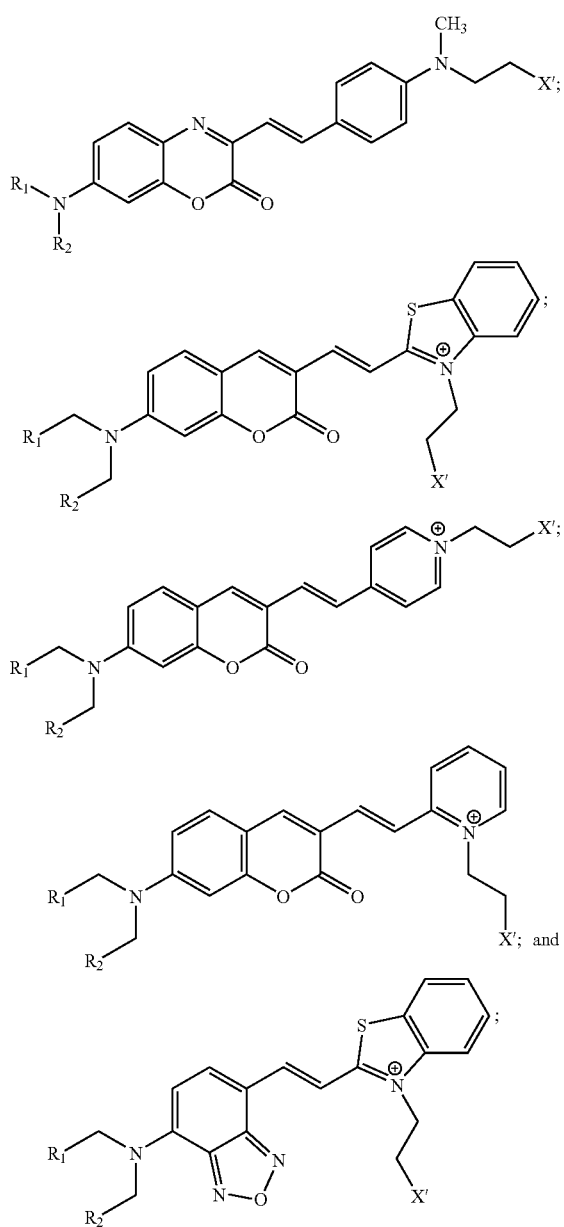

wherein X' includes hydroxyl, amino, and thiol; and $R_1$ and $R_2$ are as defined hereinabove.

In some embodiments, the presently disclosed SERS-active nanoparticles can be conjugated with a specific binding member "B" of a binding pair. The specific binding member can be conjugated with the SERS-active reporter molecule, e.g., a compound of formula A-Y through, for example, a thiol group as represented by the variable X', or bound to or otherwise associated with the nanoparticle itself. As used herein, a specific binding member is a member of a specific binding pair. A "specific binding pair" refers to two different molecules, where one of the molecules through chemical or physical means specifically binds the second molecule. In this sense, an analyte is a reciprocal member of a specific binding pair. Further, specific binding pairs can include members that are analogs of the original specific binding partners, for example, an analyte-analog having a similar structure to the analyte. By "similar" it is intended that, for example, an analyte-analog has an amino acid sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater amino acid sequence identity compared to an analyte amino acid sequence using alignment programs and standard parameters well known in the art. An analog of an analyte also can have the same function as an analyte.

In some embodiments, the binding member is a binding protein. As used herein, the term "binding protein" refers to a protein, that when conjugated with a SERS-active nanoparticle, interacts with a specific analyte or ligand in a manner capable of producing a detectable Raman signal differentiable from when a target analyte or ligand is present or absent, or when a target analyte or ligand is present in varying concentrations over time. The term "producing a detectable signal" refers to the ability to recognize a change in a property of a reporter group, e.g., a presently disclosed dye, in a manner that enables the detection of binding member-analyte, e.g., binding protein-ligand, binding. Further, the producing of a detectable signal can be reversible or non-reversible. The signal-producing event includes continuous, programmed, and episodic means, including one-time or reusable applications. The reversible signal-producing event can be instantaneous or can be time-dependent, so long as a correlation with the presence or concentration of the analyte is established.

Such embodiments can be used as a biosensor. As used herein, the terms "biosensor" and "biosensor compound" generally refer to a compound that undergoes a detectable change in specific response to a ligand or target analyte. More particularly, the presently disclosed biosensors combine the molecular recognition properties of biological macromolecules, such as a binding protein, with SERS-active nanoparticles that produce a SERS signal upon ligand binding.

The presently disclosed dye of Formula A-Y can be associated with, e.g., adsorbed, or attached, e.g., covalently bound, to a nanoparticle. Generally, the term "associated" refers to a state of two molecules or a molecule and a particle, such as a nanoparticle, being held in close proximity to one another. As provided in more detail in the Examples, the presently disclosed dyes can be mixed in an appropriate ratio with a nanoparticle solution for a few hours, e.g., four to six hours, whereby the dye is adsorbed on the nanoparticle surface. Without wishing to be bound to any one particular theory, it is believed that, in some embodiments, the presently disclosed dyes are associated with a nanoparticle through the quaternary nitrogen on the pyridinium cation, which is represented by the variable "Y."

The presently disclosed dyes can be functionalized so that the dye will bind covalently to a nanoparticle. Such embodiments can improve the stability of the dye in complex media, such as blood and serum. As used herein, the term "direct attachment" can, in some embodiments, refer to the covalent attachment of a SERS-active reporter molecule to the nanoparticle surface. Indirect attachment can be accomplished using an intervening compound, molecule, or the like. In some embodiments, the presently disclosed SERS-active reporter molecule can be modified to include a linker, such as a thiol-containing moiety, for example, the variable X' as described hereinabove, which can be directly attached to the nanoparticles, e.g., gold nanoparticles, by methods known in the art or, as disclosed in more detail herein below, a polyethylene glycol (PEG) linker. Other methods of associating the SERS-active reporter molecule, including non-covalent attachment methods known to those of ordinary skill in the art, also can be used.

A Raman enhancing nanoparticle having associated therewith, e.g., adsorbed on or attached to, a SERS-active molecule(s) is referred to herein as a SERS-active nanoparticle. More particularly, a SERS-active nanoparticle, as referred to herein, includes a nanoparticle have a surface that induces, causes, or otherwise supports surface-enhanced Raman light scattering (SERS) or surface-enhanced resonance Raman light scattering (SERRS). A number of surfaces are capable of producing a SERS signal, including roughened surfaces, textured surfaces, and other surfaces, including smooth surfaces.

"Raman scattering" generally refers to the inelastic scattering of a photon incident on a molecule. Photons that are inelastically scattered have an optical frequency ($v_i$), which is different than the frequency of the incident light ($v_0$). The difference in energy ($\Delta E$) between the incident light and the inelastically scattered light can be represented as ($\Delta E$)=h|$v_0$−$v_i$| wherein h is Planck's constant, and corresponds to energies that are absorbed by the molecule. The incident radiation can be of any frequency $v_0$, but typically is monochromatic radiation in the visible spectral region. The absolute difference |$v_0$−$v_i$| is an infrared, e.g., vibrational, frequency. The process that produces light of frequency other than $v_0$ is referred to as "Raman scattering." The frequency $v_i$ of the "Raman scattered" radiation can be greater than or less than $v_0$, but the amount of light with frequency $v_1 < v_0$ (Stokes radiation) is greater than that with frequency $v_1 > v_0$ (anti-Stokes radiation).

As used herein, the term "radiation" refers to energy in the form of electromagnetic radiation that can induce surface-enhanced Raman scattering in a sample under test, e.g., a sample comprising a SERS-active nanoparticle having one or more of the presently disclosed SERS-active reporter molecules associated therewith. More particularly, the term "radiation" refers to energy in the form of electromagnetic radiation that causes the surface of a nanoparticle to induce, emit, support, or otherwise cause light scattering, e.g., Raman scattering, in a reporter molecule proximate to the nanoparticle surface.

"Surface-enhanced Raman scattering" or "SERS" refers to the phenomenon that occurs when the Raman scattering signal, or intensity, is enhanced when a Raman-active molecule is adsorbed on or in close proximity to, e.g., within about 50 Å of, a metal surface. Under such circumstances, the intensity of the Raman signal arising from the Raman-active molecule can be enhanced. "Surface-enhanced resonance Raman scattering" or "SERRS" refers to an increased SERS signal that occurs when the reporter molecule in close proximity to the SERS-active nanoparticle surface is in resonance with the excitation wavelength.

As used herein, the terms "nanoparticle," "nanostructure," "nanocrystal," "nanotag," and "nanocomponent," are used interchangeably and refer to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm). In some embodiments, the nanoparticle is a metallic nanoparticle. In some embodiments, the nanoparticle is a spherical particle, or substantially spherical particle having a core diameter between about 2 nm and about 200 nm (including about 2, 5, 10, 20, 50, 60, 70, 80, 90, 100, and 200 nm). In some embodiments, the nanoparticle has a core diameter between about 2 nm and about 100 nm (including about 2, 5, 10, 20, 30, 40, 50, 60, 70, 80, 90, and 100 nm) and in some embodiments, between about 20 nm and 100 nm (including about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 nm). One of ordinary skill in the art, upon review of the presently disclosed subject matter, would recognize that a nanoparticle suitable for use with the presently disclosed assays can include a core, e.g., a metal core, which induces the Raman effect, and can further include one or more layers of SERS-active materials, encapsulants, and/or outer shell structures that also can contribute to the size, e.g., total diameter of the nanoparticle structure.

SERS-active nanoparticles suitable for use with the presently disclosed dyes typically comprise at least one metal, i.e., at least one element selected from the Periodic Table of the Elements that is commonly known as a metal. Suitable metals include Group 11 metals, such as Cu, Ag, and Au, or any other metals known by those skilled in the art to support SERS, such as alkali metals. In some embodiments, the nanoparticle substantially comprises a single metal element. For example, the preparation of gold nanoparticles is described by Frens, G., *Nat. Phys. Sci.*, 241, 20 (1972). In other embodiments, the nanoparticle comprises a combination of at least two elements, such as an alloy, for example, a binary alloy. In some embodiments, the nanoparticle is magnetic.

In other embodiments, the metal includes an additional component, such as in an $Au_2S$/Au core-shell particle. $Au_2S$/Au core-shell particles have been reported to have widely tunable near-IR optical resonance. See Averitt, R. D., et al., "Ultrafast optical properties of gold nanoshells," *JOSA B*, 16(10), 1824-1832 (1999). Further, Ag core/Au shell particles, such as those described by Cao, Y. W., et al., "DNA-modified core-shell Ag/Au nanoparticles," *J. Am. Chem. Soc.*, 123(32), 7961-7962 (2001), or Au core/Ag shell particles, or any core-shell combination involving SERS-active metals, can be used. Other combinations suitable for use in core-shell particles also are suitable for use with the presently disclosed subject matter, including Au- or Ag-functionalized silica/alumina colloids, Au- or Ag-functionalized $TiO_2$ colloids, Au nanoparticle capped-Au nanoparticles (see, e.g., Mucic, et al., "DNA-directed synthesis of binary nanoparticle network materials," *J. Am. Chem. Soc.*, 120(48), 12674 (1998)); Au nanoparticle-capped $TiO_2$ colloids; and particles having a Si core with a metal shell (i.e., "nanoshells"), such as silver-capped $SiO_2$ colloids or gold-capped $SiO_2$ colloids. See, e.g., Jackson, et al., *Proc. Natl. Acad. Sci. U.S.A.* 101(52):17930-5 (2004); see also U.S. Pat. Nos. 6,344,272 and 6,685,986 to Oldenburg et al., each of which is incorporated herein by reference in its entirety. The use of such nanoshells in biosensing applications has been described. See U.S. Pat. No. 6,699,724 to West et al., which is incorporated herein by reference in its entirety.

Another class of nanoparticles suitable for use with the presently disclosed SERS-active reporter molecules includes nanoparticles having an internal surface. Such nanoparticles include hollow particles and hollow nanocrystals or porous or semi-porous nanoparticles. See, e.g., U.S. Pat. No. 6,913,825 to Ostafin et al., which is incorporated herein by reference in its entirety. Accordingly, the presently disclosed subject matter also provides a nanoparticle comprising a core-shell particle active for SERS or a hollow nanoparticle active for SERS. In some embodiments, such nanoparticles can exhibit an improved SERS signal.

While it is recognized that particle shape and aspect ratio can affect the physical, optical, and electronic characteristics of nanoparticles, the specific shape, aspect ratio, or presence/absence of internal surface area does not bear on the qualification of a particle as a nanoparticle. Accordingly, nanoparticles suitable for use with the presently disclosed dyes can have a variety of shapes, sizes, and compositions. Further, the nanoparticle can be solid, or in some embodiments, as described immediately hereinabove, hollow. Non-limiting examples of suitable nanoparticles include colloidal metal hollow or filled nanobars, magnetic, paramagnetic, conductive or insulating nanoparticles, synthetic particles, hydrogels (colloids or bars), and the like. It will be appreciated by one of ordinary skill in the art that nanoparticles can exist in a variety of shapes, including but not limited to spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes.

Further, nanoparticles suitable for use with the presently disclosed dyes can be isotropic or anisotropic. As referred to herein, anisotropic nanoparticles have a length and a width. In some embodiments, the length of an anisotropic nanoparticle is the dimension parallel to the aperture in which the nanoparticle was produced. In some embodiments, the anisotropic nanoparticle has a diameter (width) of about 350 nm or less. In other embodiments, the anisotropic nanoparticle has a diameter (width) of about 250 nm or less and in some embodiments, a diameter (width) of about 100 nm or less. In some embodiments, the width of the anisotropic nanoparticle is between about 15 nm to about 300 nm. Further, in some embodiments, the anisotropic nanoparticle has a length, wherein the length is between about 10 nm and 350 nm.

Much of the SERS literature (both experimental and theoretical) suggests that anisotropic particles (rods, triangles, prisms) can provide an increased enhancement of the Raman signal as compared to spheres. For example, the so-called "antenna effect" predicts that Raman enhancement is expected to be larger at areas of higher curvature. Many reports of anisotropic particles have been recently described, including silver (Ag) prisms and "branched" gold (Au) particles.

Anisotropic Au and Ag nanorods can be produced by electrodeposition into preformed alumina templates, in a manner similar to the production of Nanobarcodes® particles (Oxonica Inc., Mountain View, Calif.). See, e.g., Nicewarner-Pena, S. R., et al., "Submicrometer metallic barcodes," *Science,* 294, 137-141 (2001); Walton, I. D., et al., "Particles for multiplexed analysis in solution: detection and identification of striped metallic particles using optical microscopy," *Anal. Chem.* 74, 2240-2247 (2002). These particles can be prepared by the deposition of alternating layers of materials, typically Au and Ag, into preformed alumina templates, and can have a diameter of about 250 nm and a length of about 6 microns.

The presently disclosed SERS-active nanoparticles also are suitable for use in composite nanostructures, e.g., satellite structures and core-shell structures, as disclosed in PCT International Patent Application No. PCT/US2008/057700 to Weidemaier et al., filed Mar. 20, 2008, which is incorporated herein by reference in its entirety.

B. Functionalized SERS-Active Nanoparticles

Further, SERS-active nanoparticles comprising the presently disclosed SERS-active dyes can be functionalized with a molecule, such as a specific binding member of a binding pair, which can bind to a target analyte. Upon binding the target analyte, the SERS spectrum of the SERS-active reporter molecule changes in such a way that the presence or amount of the target analyte can be determined. The use of a functionalized SERS-active nanoparticle has several advantages over non-functionalized nanoparticles. First, the functional group provides a degree of specificity to the nanoparticle by providing a specific interaction with a target analyte. Second, the target analyte does not have to be Raman active itself; its presence can be determined by observing changes in the SERS spectrum of the Raman-active dye attached to the nanoparticle. Such measurements are referred to herein as "indirect detection," in which the presence or absence of a target analyte or ligand in a biological sample is determined by detecting a SERS signal that does not directly emanate from the target analyte or ligand of interest.

The presently disclosed SERS-active nanoparticles can be functionalized to bind to a target analyte in at least two different ways. In some embodiments, the SERS-active reporter molecule, i.e., the SERS-active dye, can be conjugated with a specific binding member of a binding pair, whereas in other embodiments, a specific binding member of a binding pair can be attached directly to the nanoparticle. In embodiments in which the nanoparticle core is at least partially surrounded by an encapsulating shell, the binding member can be attached to an outer surface of the encapsulating shell.

1. Functionalized SERS-Active Nanoparticles Associated with SERS-Active Reporter Molecules Conjugated with Specific Binding Members of a Binding Pair In some embodiments, the SERS-active near-IR dye associated with a SERS-active nanoparticle can be functionalized to bind to a target analyte. Such functionalized SERS-active nanoparticles can be used in combination with binding assays to detect physiologically important molecules, including metabolites, such as glucose, lactate, and fatty acids, in biological samples. In some embodiments, the presently disclosed SERS-active dyes include a reactive group that can be used to couple or conjugate the dye with another molecule, including a member of a specific binding pair, such as a binding protein or a receptor, which has an affinity for a specific ligand or analyte.

In some embodiments, the dye nucleus can include a thiol-reactive group that can be conjugated to the thiol moiety of a cysteine amino acid residue in a natural or an engineered or mutated protein. As used herein, the term "thiol-reactive group" refers to a substituent group that can react with a thiol moiety to form a carbon-sulfur bond. Examples of suitable thiol-reactive groups that can be introduced into the presently disclosed dyes include a halo-acetyl group and a halo-acetamide group. In some embodiments, the halo-acetyl group includes an iodoacetyl group, whereas the halo-acetamide group can include an iodoacetamide or bromoacetamide group. One of ordinary skill in the art upon review of the presently disclosed subject matter would recognize that other thiol-reactive groups known in the art, such as maleimide groups, are suitable for use with the presently disclosed subject matter.

As used herein, the term "conjugate" refers to a molecule comprising two or more subunits bound together, optionally through a linking group, to form a single molecular structure. The binding can be made either by a direct chemical bond between the subunits or through a linking group. Such binding in a conjugate typically is irreversible. As used herein, the term "affinity" refers to the strength of the attraction between one binding member to another member of a binding pair at a particular binding site. The term "specificity" and derivations thereof, refer to the likelihood that a binding member will bind to another member of a binding pair. Such binding between one binding member, e.g., a binding protein, to another binding member of a binding pair, e.g., a ligand or analyte, can be reversible.

The term "specific binding member" refers to a molecule for which there exists at least one separate, complementary binding molecule. A specific binding member is a molecule that binds, attaches, or otherwise associates with a specific molecule. The binding, attachment, or association can be chemical or physical. A specific molecule to which a specific binding member binds can be any of a variety of molecules, including, but not limited to, antigens, haptens, proteins, carbohydrates, nucleotide sequences, nucleic acids, amino acids, peptides, enzymes, and the like. Further, a specific binding member of a particular type will bind a particular type of molecule. In such instances, the specific binding members are referred to as a "specific binding pair." Accordingly, an antibody will specifically bind an antigen. Other specific binding pairs include avidin and biotin, carbohydrates and lectins, complementary nucleotide sequences, complementary peptide sequences, enzymes and enzyme cofactors, and the like.

Representative specific binding members of a binding pair are disclosed in more detail herein below.

2. SERS-Active Nanoparticles Having a Specific Binding Member of a Binding Pair Attached Directly Thereto In some embodiments, a binding member of a specific binding pair, for example, an antibody, such as a monoclonal antibody, can be attached directly to the surface of the nanoparticle or to the outer surface of a shell encapsulating the nanoparticle. In an exemplary embodiment, a specific binding member of a binding pair, e.g., a monoclonal antibody, can be treated with linker, e.g., polyethylene glycol (PEG), and attached directly to the nanoparticle through the PEG linker. Use of a linker, such as a PEG linker, allows the native properties and structure of the specific binding member to be retained and increases the specificity of the functionalized nanoparticle by sterically hindering non-specific binding of other species to the nanoparticle. SERS-active nanoparticles having a specific binding member attached through a PEG linker are described in more detail herein (see Section I.D., herein below).

Depending on the binding member, one of ordinary skill in the art would recognize upon review of the presently disclosed subject matter that linkers other than PEG can be used. For example, alkanethiols can be used as linkers for antibodies and peptides. Short chain alkanethiols, including, but not limited to, N-succinimidyl-S-acetylthioacetate (SATA) and N-succinimidyl-S-acetylthiopropionate (SATP) can be used as linkers after sulfhydryl deprotection. Other properties also can determine the choice of linker, such as the length of the linker chain. For example, PEG can be desirable in that it also acts to protect the surface of the reagent and is flexible, which can enhance the ability of the reagent to bind to the analyte of interest.

Nanoparticles having one or more SERS-active reporter molecules and specific binding members attached thereto can be disposed in an appropriate medium, e.g., a buffered solution, to provide a SERS-active reagent.

3. Representative Binding Members

In some embodiments, the binding member conjugated with the presently disclosed SERS-active nanoparticle, either through the SERS-active reporter molecule or directly attached to an outer surface of the nanoparticle itself, comprises a polypeptide or protein. Representative binding proteins suitable for use with the presently disclosed SERS-active nanoparticles, include, but are not limited to periplasmic binding proteins (PBPs). Examples of PBPs include, but are not limited to, glucose-galactose binding protein (GGBP), maltose binding protein (MBP), ribose binding protein (RBP), arabinose binding protein (ABP), dipeptide binding protein (DPBP), glutamate binding protein (GluBP), iron binding protein (FeBP), histidine binding protein (HBP), phosphate binding protein (PhosBP), glutamine binding protein (QBP), oligopeptide binding protein (OppA), or derivatives thereof, as well as other proteins that belong to the families of proteins known as periplasmic binding protein like I (PBP-like I) and periplasmic binding protein like II (PBP-like II). For other binding proteins suitable for use with the presently disclosed SERS-active nanoparticles, see U.S. Patent Application Publication Nos. 2006/0078908 and 2006/0280652 to Pitner et al. and U.S. patent application Ser. No. 11/738,442, filed Apr. 20, 2007, each of which is incorporated herein by reference in its entirety.

Other examples of proteins that can comprise the binding members include, but are not limited to intestinal fatty acid binding proteins (FAPBs). The FABPs are a family of proteins that are expressed at least in the liver, intestine, kidney, lungs, heart, skeletal muscle, adipose tissue, abnormal skin, adipose, endothelial cells, mammary gland, brain, stomach, tongue, placenta, testis, and retina. The family of FABPs is, generally speaking, a family of small intracellular proteins (about 14 kDa) that bind fatty acids and other hydrophobic ligands through non-covalent interactions. See Smith, E. R. and Storch, J., *J. Biol. Chem.*, 274 (50):35325-35330 (1999), which is incorporated herein by reference in its entirety. Members of the FABP family of proteins include, but are not limited to, proteins encoded by the genes FABP1, FABP2, FABP3, FABP4, FABP5, FABP6, FABP7, FABP(9) and MP2. Proteins belonging to the FABP include I-FABP, L-FABP, H-FABP, A-FABP, KLBP, mal-1, E-FABP, PA-FABP, C-FABP, S-FABP, LE-LBP, DA11, LP2, Melanogenic Inhibitor, and the like.

Other binding members include specific binding members having an affinity for a target analyte, including antibodies for target analytes, such as prostate specific antigen (PSA), creatine kinase MB (CKMB) isoenzyme, cardiac troponin I (cTnI) protein, thyroid-stimulating hormone (TSH), influenza A (Flu A) antigen, influenza B (Flu B) antigen, and respiratory syncytial virus (RSV) antigen. Antibodies for such target analytes are known in the art.

As used herein, a "derivative" of a protein or polypeptide is a protein or polypeptide that shares substantial sequence identity with the wild-type protein. Derivative proteins or polypeptides of the presently disclosed subject matter can be made or prepared by techniques well known to those of skill in the art. Examples of such techniques include, but are not limited to, mutagenesis and direct synthesis. Derivative proteins also can be modified, either by natural processes, such as post-translational processing, or by chemical modification techniques which are well known in the art. Such modifications are well described in basic texts and in more detailed monographs, as well as in voluminous research literature. Modifications can occur anywhere in the polypeptide chain, including the peptide backbone, the amino acid side-chains and the amino or carboxyl termini. It will be appreciated that the same type of modification can be present in the same or varying degrees at several sites in a given polypeptide or protein. Also, a given polypeptide or protein can contain more than one modification. Examples of derivative proteins include, but are not limited to, mutant and fusion proteins.

A "mutant protein" is used herein as it is known in the art. In general, a mutant protein can be created by addition, deletion or substitution of the wild-type primary structure of the protein or polypeptide. Mutations include, for example, the addition or substitution of cysteine groups, non-naturally occurring amino acids, and replacement of substantially non-reactive amino acids with reactive amino acids. A mutant protein can be mutated to bind more than one analyte in a specific manner. Indeed, the mutant proteins can possess specificity towards its wild-type analyte and another target ligand. Likewise, a mutant protein can be able to only bind an analyte or analytes that the wild-type binding protein does not bind. Methods of generating mutant proteins are well-known in the art. For example, Looger, L. L., et al., *Nature* 423 (6936): 185-190 (2003), which is incorporated herein by reference, disclose methods for redesigning binding sites within periplasmic binding proteins that provide new analyte-binding properties for the proteins. These mutant binding proteins retain the ability to undergo conformational change, which can produce a directly generated signal upon analyte-binding. By introducing between 5 and 17 amino acid changes, Looger, et al. constructed several mutant proteins, each with new selectivities for TNT (trinitrotoluene), L-lactate, or serotonin.

The mutation can serve one or more of several purposes. For example, a naturally occurring protein can be mutated to change the long-term stability, including thermal stability, of the protein, to conjugate the protein to a particular encapsulation matrix or polymer, to provide binding sites for detectable reporter groups, to adjust its binding constant with respect to a particular analyte, or combinations thereof.

The analyte and mutated protein can act as binding partners. The term "associates" or "binds" as used herein refers to binding partners having a relative binding constant (Kd) sufficiently strong to allow detection of binding to the protein by a detection means. The Kd can be calculated as the concentration of free analyte at which half the protein is bound, or vice versa. When the analyte of interest is glucose, the Kd values for the binding partners are between about 0.0001 mM and about 50 mM.

The presently disclosed SERS-active reporter molecule can be attached to a mutated protein, for example a GGBP, by any conventional means known in the art. For example, the reporter molecule can be conjugated to the protein via amines or carboxyl residues on the protein. Exemplary embodiments include covalent coupling via thiol groups on cysteine residues of the mutated or native protein. For example, for mutated GGBP, cysteines can be located at position 10, at position 11, position 14, at position 15, position 19, at position 26, at position 43, at position 74, at position 92, at position 93, position 107, position 110, position 112, at position 113, at position 137, at position 149, at position 152, at position 154, at position 182, at position 183, at position 186, at position 211, at position 213, at position 216, at position 238, at position 240, at position 242, at position 255, at position 257, at position 287, at position 292, at position 294, and at position 296.

C. Encapsulated SERS-Active Nanoparticles

SERS-active metal nanoparticles have a tendency to aggregate in aqueous solution and once aggregated are difficult to re-disperse. Further, the chemical composition of some Raman-active molecules is incompatible with chemistries used to attach other molecules, such as proteins, to metal nanoparticles. These characteristics can limit the choice of Raman-active molecule, attachment chemistries, and other molecules to be attached to the metal nanoparticle.

Accordingly, in some embodiments, the presently disclosed SERS-active dye of Formula A-Y when affixed, e.g., either adsorbed or covalently attached to a nanoparticle, can be coated or encapsulated, for example, in a shell, of a different material, including a polymer, glass, or ceramic material. Such embodiments are referred to herein as "composite SERS-active nanoparticles." Methods for preparing composite SERS-active nanoparticles are described in U.S. Pat. No. 6,514,767 to Natan, which is incorporated herein by reference in its entirety.

The presently disclosed composite SERS-active nanoparticles can include a metal nanoparticle, a submonolayer, monolayer, or multilayer of one or more presently disclosed dyes in close proximity to the surface of the metal nanoparticle. The term "in close proximity" is intended to mean within about 50 nm or less of an outer surface of the nanoparticle. A nanoparticle having a submonolayer, monolayer, or multilayer of one or more presently disclosed dyes attached to an outer surface of the nanoparticle core also can include an encapsulating shell. In such embodiments, the presently disclosed dye is positioned at an interface between the outer surface of the metal nanoparticle and an interior surface of the encapsulating shell.

The nanoparticle core comprising the composite nanoparticle can be a metal sphere, e.g., a gold, silver, or copper sphere, having a diameter of about 20 nm to about 200 nm. In some embodiments, the nanoparticle core comprises an oblate or prolate metal spheroid. The diameter of the nanoparticle core can be selected based, in part, on the wavelength of incident light. For example, in SERS using red incident light, i.e., incident light having a wavelength of about 600 nm, the optimal SERS response is obtained with gold nanoparticle cores having a diameter of about 60 nm.

In some embodiments, the encapsulating shell comprises a dielectric material, such as a polymer, glass, metal, metal oxides, such as $TiO_2$ and $SnO_2$, metal sulfides or a ceramic material. In some embodiments, the encapsulant is glass, e.g., $SiO_x$. To encapsulate the presently disclosed SERS-active nanoparticles in glass, the metal nanoparticle cores can be treated with a glass primer, i.e., a material that can lead to a growth of a uniform coating of glass, or can improve adhesion of the glass coat to the particle, or both. Glass can then be grown over the metal nanoparticle by standard techniques known in the art.

The encapsulation process can be carried out after, or during, attaching or adsorbing one or more presently disclosed dyes to the core nanoparticle. In this way, the dye is sequestered from the surrounding solvent as a coating on the surface of the metal nanoparticle core. Such a configuration provides the metal nanoparticle core with a stable SERS activity. The dye can form a sub-monolayer, a complete monolayer, or a multilayer assembly on the surface of the metal nanoparticle core. The dye layer can comprise a single dye or can be a mixture of different dyes.

Thus, in some embodiments, the SERS-active reporter molecule of formula A-Y forms a layer on the outer surface of the nanoparticle core, wherein the layer at least partially covers the outer surface of the nanoparticle core and is defined by an inner surface and an outer surface. The encapsulant is disposed on at least one of the outer surface of the nanoparticle core and the outer surface of the layer of the SERS-active reporter molecule of formula A-Y to at least partially surround the nanoparticle core, which is at least partially covered with a layer of the SERS-active reporter molecule.

Preferably, the encapsulant does not measurably alter the SERS activity of the composite SERS-active nanoparticle. The benefits of the presently disclosed subject matter are still achieved, however, even if the encapsulant has some measurable effect, provided it does not interfere with the SERS activity, or does not add significant complexity to the observed SERS spectrum.

Further, in some embodiments, the encapsulant can be modified, e.g., derivatized by standard techniques known in the art, to attach molecules, including biomolecules, to its outer surface. This characteristic allows the presently disclosed composite SERS-active nanoparticles to be conjugated to molecules, including biomolecules, such as proteins and nucleic acids, or to solid supports without interfering with the Raman activity of the dye. Glass and other materials suitable for use as an encapsulating shell contain functional groups amenable to molecular attachment. For example, immersion of glass in a suitable base allows for the covalent attachment of alkyl trichlorosilanes or alkyl trialkoxysilanes, with additional functionality available on the end of the alkyl group of the alkyl trichlorosilane or alkyl trialkoxysilane group. Thus, glass surfaces can be modified with many forms of biomolecules and biomolecular superstructures, including cells, as well as oxides, metals, polymers, and the like. Likewise, surfaces of glass can be modified with well-organized monomolecular layers. Accordingly, glass coatings support many types of chemical functionalization (also referred to herein as "derivatization"). Other forms of encapsulants also can be functionalized, as well. Accordingly, the presently disclosed nanoparticles can be affixed to any species known in the art having a chemically-reactive functionality.

The thickness of the encapsulant can be varied depending on the physical properties required of the SERS-active nanoparticle. Depending on the particular combination of nanoparticle core, encapsulant, and dye, thick coatings of encapsulant, e.g., coatings on the order of one micron or more, could potentially attenuate the Raman signal. Further, a thin coating might lead to interference in the Raman spectrum of the analyte by the molecules on the encapsulant surface. At the same time, physical properties, such as the sedimentation coefficient can be affected by the thickness of the encapsulant. In general, the thicker the encapsulant, the more effective the sequestration of the SERS-active dyes on the metal nanoparticle core from the surrounding solvent.

In embodiments wherein the encapsulant is glass, the thickness of the glass typically can range from about 1 nm to about 50 nm. In exemplary, non-limiting embodiments, the encapsulated SERS-active nanoparticles comprise gold nanoparticles having a diameter ranging from about 50 nm to about 100 nm encapsulated in a sphere of glass having a thickness ranging from about, in some embodiments, from about 10 nm to about 50 nm; in some embodiments, from about 15 nm to about 40 nm; and, in some embodiments, about 35 nm. The optimization of the dimensions of the presently disclosed encapsulated SERS-active nanoparticles can be accomplished by one of ordinary skill in the art. For example, it is known in the art that core-shell nanoparticles (e.g., Au/AuS nanoparticles) support SERS and have different optical properties as compared to pure metal nanoparticles. Likewise, it is known in the art that SERS from prolate spheroids can be enhanced relative to spheres with the same major axis. Further, it is known that single particle enhancements are wavelength-dependent. Thus, the particle size can be "tuned" to achieve a maximum SERS signal for a given excitation wavelength. Accordingly, the composition of the particle, or its size or shape can be altered in accordance with the presently disclosed subject matter to optimize the intensity of the SERS signal.

The presently disclosed composite SERS-active nanoparticles are easy to handle and store. Further, they also are aggregation resistant, stabilized against decomposition of the dye in solvents and air, are chemically inert, and can be centrifuged, concentrated, e.g., by magnetic pull down techniques, and redispersed without loss of SERS activity. Unlike metal nanoparticles, the presently disclosed composite SERS-active nanoparticles can be evaporated to dryness, and then completely redispersed in solvent.

D. Polyethylene Glycol (PEG) Linkers

In some embodiments, a polyethylene glycol (PEG) linker can be used to attach a specific binding member to a SERS-active nanoparticle, a magnetic capture particle (in magnetic capture assays), or to a solid support (in heterogeneous assays). The use of a PEG linker can reduce non-specific binding in the presently disclosed assays. Eliminating non-specific adsorption can be a significant challenge to assay performance. For example, in magnetic capture assays, non-specific binding can include the process in which proteins or other biomolecules from solution adhere to the surfaces of the magnetic capture particle or SERS-active nanoparticle, thereby presenting binding members for the target analyte or the process by which the surfaces of the magnetic capture particle and SERS-active nanoparticle adhere to one another via non-specific interactions.

More generally, non-specific binding refers to binding between molecules that is relatively independent of specific surface structures. Non-specific binding can be distinguished from specific binding, which involves the specific recognition of one of two different molecules for the other compared to substantially less recognition of other molecules. The nature of the molecule or molecules that result in non-specific binding in liquid-based assays depends on the nature of the sample, the assay milieu, the nanoparticle surface, and the like.

Non-specific binding can be attributed to at least two different mechanisms, each of which can interfere with an assay. First, non-specific adsorption of biological materials to a SERS-active nanoparticle or a magnetic capture nanoparticle can sterically hinder the association of the binding molecule with the analyte, resulting in a false-negative result or an underestimation of the analyte concentration in a quantitative assay. By "adsorption" is intended the accumulation of solutes, biological compounds or other solid materials on the surface of a solid or the adhesion of a layer of molecules of some substance to the surface of a solid.

Second, non-specific association between magnetic capture particles and SERS-active nanoparticles, particularly those that have been functionalized, can increase the baseline levels of the assay in the absence of analyte, leading to a reduction in the sensitivity level of the assay and limiting the dynamic range. This baseline increase can result in a reduction in the minimum level of analyte that can be detected in a sample. This non-specific association between the nanoparticles, particularly nanoparticles in solution, also can lead to non-specific aggregation of the particles.

Strategies known in the art for blocking non-specific binding generally involve one of three approaches. In one approach, the surface can be treated with proteins, e.g., albumin, ovalbumin, fish gelatin, and casein, powdered milk, and/or blocking buffer. Drawbacks to this approach include a lack of complete blocking of non-specific adsorption, see, e.g., Taylor, S., et al., "Impact of Surface Chemistry and Blocking Strategies on DNA Microarrays," *Nucleic Acids Research*, 31(16), e87 (2003), which is incorporated herein by reference in its entirety; the need to optimize blocking conditions for each new assay; and a varying performance from lot to lot of blocking agent. Such blocking steps also add an additional step to the assay, which increases the complexity and duration of the assay.

A second approach involves adding detergents or other chemical agents to the assay buffer. This approach also suffers from the need to optimize conditions and reagents for each new assay and can interfere with the specific biomolecular interactions the assay is intended to detect.

Another approach involves coating the surface of the solid support, nanoparticle, or magnetic particle with a polymer, such as polyethylene glycol. Without wishing to be bound to any one particular theory, it is thought that the reduction in non-specific adsorption brought about by PEG-coated surfaces is a result of PEG molecules having hydrophilic properties and having many rotational degrees of freedom. In an aqueous environment, the PEG chains are surrounded by water molecules. These conditions result in a high level of entropy for the PEG molecules. Adsorption of a biomolecule, e.g., a protein, onto a PEG-coated surface compresses the PEG chains, thereby displacing water molecules and imparting order on the PEG chains. This ordering can result in a thermodynamically unfavorable drop in entropy resulting in the resistance of biomolecule adsorption on PEG-coated surfaces. Although the coating of two-dimensional surfaces by a polymer, such as PEG, can be effective in reducing non-specific binding, none of the previously utilized approaches are effective in reducing non-specific aggregation of three-dimensional particles in solution. See Dubertret, B., et al., "In Vivo Imaging of Quantum Dots Encapsulated in Phospholipid Micelles," *Science,* 298, 1759-1762 (2002), which is incorporated herein by reference in its entirety.

The presently disclosed subject matter demonstrates that non-specific adsorption of biological materials to the nanoparticle or associations between the nanoparticles, or both, can be reduced through the use of the presently disclosed PEG linker (see Experimental Example 3). The presently disclosed method is general to blocking non-specific binding. Thus, the need to optimize blocking conditions for individual assays has been largely eliminated. Because polyethylene glycol (PEG)-based molecules are non-ionic, the detrimental effect of pH and salt concentration on the ability of PEG to resist non-specific protein adsorption is thought to be minimal.

In some embodiments, the PEG linker comprises a bifunctional PEG molecule having a functional group on either terminal end of the linear molecule, separated by two or more ethylene glycol subunits. In some embodiments, the PEG molecule comprises between 2 and about 1000 ethylene glycol subunits, including but not limited to, 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 40, at least 50, at least 60, at least 70, at least 80, at least 90, at least 100, at least 200, at least 300, at least 400, at least 500, at least 600, at least 700, at least 800, at least 900, or at least 1000 ethylene glycol subunits. In certain embodiments, the PEG molecule comprises between about 10 to about 100 ethylene glycol subunits, and in particular embodiments, at least 12 ethylene glycol subunits.

The PEG linker can have a molecular weight of about 200 Da to about 100,000 Da, including but not limited to, about 200, about 500, about 1,000 Da, about 2,000 Da, about 3,000 Da, about 4,000 Da, about 5,000 Da, about 6,000 Da, about 7,000 Da, about 8,000 Da, about 9,000 Da, about 10,000 Da, about 20,000 Da, about 50,000 Da, about 75,000 Da, and about 100,000 Da. It is to be understood, however, that PEG linkers of higher or lower molecular weights can be used with the presently disclosed subject matter depending on the particular application. In certain embodiments, the PEG linker has a molecular weight of about 5,000 Da or greater. For a given surface density of PEG molecules, longer PEG chains, e.g., a PEG linker with a molecular weight equal to or greater than about 5,000 Da, can be more effective at reducing non-specific adsorption in binding assays than shorter chains. Longer PEG chains also can position a binding member, e.g., an antibody or DNA probe further away from the particle surface. Such embodiments can minimize "folding back" of antibodies onto the particle surface, which can reduce the number of available analyte (e.g., antigen) binding sites.

The bifunctional PEG linker comprises functional groups on each terminal end of the molecule and these functional groups can be used to attach a specific binding member to one end of the PEG molecule and a SERS-active nanoparticle (or magnetic capture particle) to the other end. The specific binding member can first be attached to the bifunctional PEG linker, followed by attachment of the specific binding member-PEG conjugate to the nanoparticle. Alternatively, the bifunctional PEG linker can be attached to the nanoparticle prior to attachment of the specific binding member to the PEGylated nanoparticle.

It is to be noted that a PEG linker also can be used to attach a SERS-active dye to the nanoparticle surface or to attach a specific binding member to a magnetic capture particle, such as a magnetic particle used in a magnetic capture liquid-based SERS assay.

The functional groups on each terminal end of the PEG linkers can be selected based on the nanoparticle surface chemistry and the desired functionality for attachment of the specific binding member (or SERS-active dye). Non-limiting examples of useful functional groups on PEG linkers include active esters of carboxylic acid or carbonate derivatives, particularly those in which the leaving groups are N-hydroxysuccinimide, p-nitrophenol, imidazole or 1-hydroxy-2-nitrobenzene-4-sulfonate. Thiol-reactive groups, including maleimido or haloacetyl groups are useful for the modification of free sulfhydryl groups on proteins or for reacting with thiol groups, such as those that might be present on the surface of SERS-active nanoparticles.

In addition, amino hydrazine or hydrazide groups on PEG molecules are useful for reaction with aldehydes generated by periodate oxidation of carbohydrate groups. This attachment chemistry is particularly useful for the site-directed attachment of antibodies onto a particle. For example, a bifunctional PEG linker comprising a hydrazine or hydrazide group at one terminal end can be used to attach an antibody to the surface of a SERS-active nanoparticle through the oligosaccharide moieties on the antibody, which are primarily present in the Fc portion of IgG molecules. In this way, the functionalized nanoparticle can be designed to maximize the presentation of the antigen binding region to the test solution, thereby potentially increasing the sensitivity of the assay. In fact, site-directed immobilization of IgG molecules via the oligosaccharide moieties to hydrazide-derivatized solid supports has been demonstrated to enhance antigenic affinity by about three times over those IgG molecules immobilized through other types of attachment chemistries, such as via IgG lysine residues, which are present throughout the antibody molecule. See O'Shannessy, D. J. and Hoffman, W. L., *Biotechnol. Appl. Biochem.* 9, 488-496 (1987); Hoffman, W. L. and O'Shannessy, D. J., *J. Immunol. Method,* 112, 113-120 (1988).

The bifunctional PEG linker molecule can be homobifunctional or heterobifunctional. As used herein, the term "homobifunctional" refers to a PEG linker molecule in which the terminal functional groups are the same. The term "heterobifunctional" refers to a PEG linker molecule in which the terminal functional groups are different from each other. Thus, in some embodiments, the PEG linker molecule comprises a heterobifunctional PEG molecule comprising a first functional group at a first terminal end and a second functional group at a second terminal end of the PEG molecule. In some of these embodiments, the first functional group at the first terminal end of the heterobifunctional PEG molecule comprises a N-hydroxysuccinimide (NHS)-ester. In certain embodiments, the second functional group at the second terminal end of the heterobifunctional PEG molecule comprises a maleimide group. Thus, in particular embodiments, the heterobifunctional PEG molecule comprises a NHS-ester at the first terminal end and a maleimide group at the second terminal end.

In those embodiments in which the specific binding member comprises a polynucleotide (e.g., an oligonucleotide), the polynucleotide can be attached to the PEG molecule via an amine group at the 5'-terminal or 3'-terminal end of the polynucleotide, which can react with a PEG molecule that comprises an amine-reactive N-hydroxysuccinimide-ester to form an amino ester (peptide) linkage between the polynucleotide and the PEG linker.

In some embodiments, thiol groups on the surface of a SERS-active nanoparticle are reacted with a thiol-reactive maleimide group on the PEG linker to form a carbon-sulfur bond. In some of these embodiments, the PEG linker comprises a heterobifunctional PEG linker comprising an amine-reactive N-hydroxysuccinimide-ester on one terminal end and a maleimide group on the other terminal end.

In some embodiments, a bifunctional PEG linker can be used to attach specific binding members to the SERS-active nanoparticles or magnetic particles and the remaining functional groups on the surface of the nanoparticle or magnetic particle can be bound by additional PEG molecules (e.g., monofunctional PEG molecules) to protect these groups from interacting non-specifically with molecules within the test sample or other particles. One of ordinary skill in the art upon review of the presently disclosed subject matter would recognize that any PEG architecture, including, but not limited to, linear polymers, star polymers or copolymers involving PEG, could be used for this purpose.

Further, monofunctional PEG molecules can be used to coat nanoparticles or magnetic particles comprising a specific binding member that has been attached thereto with other types of immobilization chemistries known in the art. For example, streptavidin-biotin coupling chemistry can be used to attach specific binding members to the particle surface, whereas PEG molecules, e.g., maleimide-activated PEG molecules, can be used to block non-specific adsorption on a thiolated SERS particle surface.

II. Applications of the Presently Disclosed SERS-Active Nanoparticles

In some embodiments, a SERS-active nanoparticle comprising the presently disclosed SERS-active reporter molecules can be used in a diagnostic assay for determining the presence or amount of an analyte or ligand of interest in a biological sample. Representative diagnostic assays and methods in which the presently disclosed SERS-active nanoparticles are applicable are disclosed in PCT International Patent Application No. PCT/US2008/057700 to Weidemaier et al., filed Mar. 20, 2008, which is incorporated herein by reference in its entirety. Accordingly, in some embodiments, the presently disclosed subject matter provides assay methods, compositions, and kits including SERS-active nanoparticles comprising the presently disclosed SERS-active reporter molecules.

In some embodiments, a SERS-active nanoparticle comprising the presently disclosed SERS-active reporter molecules can be used to detect one or more of a nucleic acid, e.g., deoxyribonucleic acid (DNA), a DNA fragment, a nucleotide, a polynucleotide, an oligonucleotide, and the like. Generally, the method comprises contacting one or more of a nucleic acid, a DNA fragment, a nucleotide, a polynucleotide, an oligonucleotide, with a presently disclosed SERS-active nanoparticle having an oligonucleotide attached thereto and detecting the presence of or a change in the SERS spectrum thereof.

Further, in some embodiments, a SERS-active nanoparticle comprising the presently disclosed reporter molecules can be used in cellular imaging. In such embodiments, the presently disclosed SERS-active nanoparticles, for example, a SERS-active nanoparticle labeled with a binding member of a specific binding pair, can be incorporated into cells or tissues and SERS can be used to characterize the distribution of the nanoparticles therein. Such embodiments can be used to distinguish between normal and abnormal, e.g., cancerous, cells.

A. Diagnostic Assays

In some embodiments, nanoparticles having one or more presently disclosed SERS-active reporter molecules attached thereto can be used in diagnostic assays. For example, Rohr et al. demonstrated an immunoassay with SERS detection including multiple components and washing steps. See Rohr, T. E., et al., "Immunoassay employing surface-enhanced Raman spectroscopy," Anal. Biochem., 182:388 (1989). Also, Ni et al. demonstrated reporter attachment to a gold slide in a heterogeneous detection assay including incubation and washing steps. See Ni, J., et al., "Immunoassay Readout Method Using Extrinsic Raman Labels Adsorbed on Immunogold Colloids," Anal. Chem., 71:4903 (1999). The SERS assays disclosed by Rohr et al. and Ni et al., as well as others known in the art, require lengthy incubations and wash steps.

Another example of an assay using SERS is disclosed in U.S. Pat. No. 5,266,498 to Tarcha et al., which is incorporated herein by reference in its entirety. Tarcha et al. discloses the use of a multiple reagent system in which a label or antibody is attached to a SERS surface. A second reagent contains the complementary pair of either label or antibody.

In some embodiments, the presently disclosed SERS-active nanoparticles can be used in a so-called "liquid-based assay." Liquid-based assay approaches using SERS-active nanoparticles have been previously disclosed. See, e.g., Hirsch et al., "A Whole Blood Immunoassay Using Gold Nanoshells," Anal. Chem., 75 (10), 2377-2381 (2003), which is incorporated herein by reference in its entirety. Hirsch et al. discloses the optical detection of particle aggregation in the presence of an analyte of interest by measuring optical absorption changes due to particle interactions. The aggregation of the nanoparticles in the assay disclosed by Hirsch et al. detects the plasmon resonance decrease that occurs as a result of the aggregation of particles. Hirsch et al., however, does not disclose the use of Raman signals for detection.

In one embodiment of the presently disclosed assays, SERS-active particles can be used in a so-called "no-wash" or "homogeneous" assay. In such an assay, a sample is collected into a container, e.g., a specimen collection container, an assay vessel, or other sample container suitable for use with the presently disclosed assays, and the assay is performed without the need to remove sample from the container, e.g., an assay vessel. Advantageously, the sample can be collected into a container that can already contain all reagents necessary to perform the assay. In some embodiments, however, one or more reagents can be added to the container following specimen collection.

In liquid-based assays, the sample typically is incubated, e.g., at ambient conditions, but it also is possible to provide controlled conditions, such as a specific temperature or rocking of the sample. Following the incubation period, the container can then placed into a reader to obtain a signal from one or more SERS-active particles that were pre-loaded or subsequently added into the container. A Raman signal is produced, and detected, upon interrogation by incident radiation of a particular wavelength, e.g., laser radiation.

In other embodiments, the presently disclosed SERS-active nanoparticles can be used in heterogeneous assays. As used herein, the term "heterogeneous assay" generally refers to an assay in which one or more components of the assay are added or removed from the assay sequentially. More particularly, a heterogeneous assay can rely, in part, on the transfer of analyte from a liquid sample to a solid phase by the binding of the analyte during the assay to the surface of the solid phase. At some stage of the assay, whose sequence varies depending on the assay protocol, the solid phase and the liquid phase are separated and the determination leading to detection and/or quantitation of the analyte is performed on one of the two separated phases. Thus, a heterogeneous assay, for example, can include a solid support coated with an antigen or antibody that binds an analyte of interest and thereby separates or removes the analyte from other components in the sample under test. These other components can be selectively removed from the sample by one or more washing steps and the analyte remains bound to the solid support, where it is detected, or can be removed by an additional washing step and subsequently detected.

Generally, the presently disclosed SERS-active nanoparticles can be used in immunoassays when conjugated to an antibody against a target molecule of interest. In some embodiments, the presently disclosed dyes can be attached, e.g., covalently attached to a nanoparticle, and used in a diagnostic assay where the intensity of the SERS signal arising from the dye changes as a function of the amount of analyte, e.g., proteins, nucleic acids, and metabolites, detected. Further, in some embodiments, the nanoparticles labeled with the presently disclosed dyes also can be labeled with another species, such as a specific member of a binding pair, for example, an antibody, to facilitate the detection of one or more analytes in a sample under test. Nanoparticles having the presently disclosed dyes associated with or attached thereto can be used in assays, for example, biological or chemical assays, in which a detectable label is required.

In some embodiments, the presently disclosed subject matter provides a method for detecting the presence or amount of one or more analytes in a biological sample, the method comprising:

(a) providing a biological sample suspected of containing one or more analytes;

(b) contacting the biological sample with a reagent comprising one or more SERS-active nanoparticles having associated therewith at least one specific binding member having an affinity for the one or more analytes and at least one SERS-active reporter molecule of Formula:

A-Y wherein:

A is selected from the group consisting of:

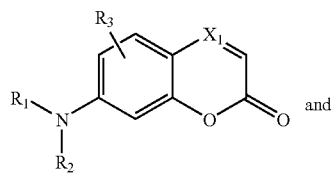

and

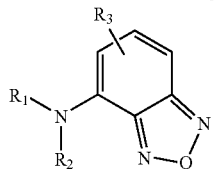

wherein $X_1$ is $CR_4$ or N;

Y is selected from the group consisting of:

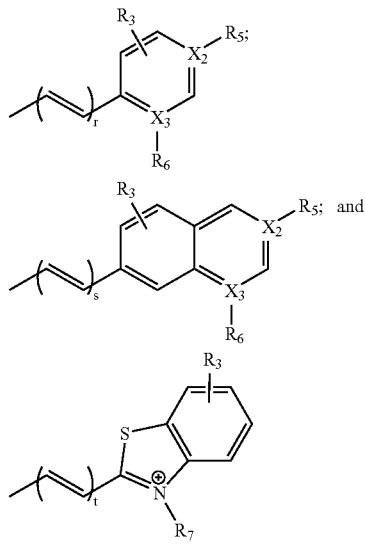

wherein:

r, s, and t are each independently an integer from 1 to 8;

each $X_2$ and $X_3$ is independently selected from the group consisting of C, S, and N, under the proviso that (i) when $X_2$ is C or S, $R_5$ is Z, or when $X_3$ is C or S, $R_6$ is Z, as Z is defined herein below; (ii) if both $X_2$ and $X_3$ are N at the same time, at least one of $R_5$ and $R_6$ is absent; and (iii) when $X_2$ is N, $R_5$ when present is Z', or when $X_3$ is N, $R_6$ when present is Z', wherein Z' is selected from the group consisting of:

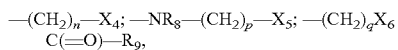

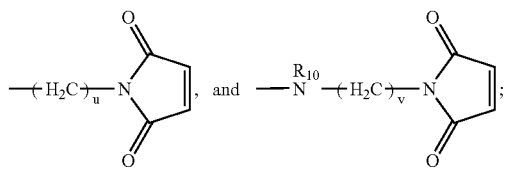

wherein:

n, p, q, u, and v are each independently an integer from 1 to 8;

$X_4$ and $X_5$ are each independently selected from the group consisting of hydroxyl, amino, and thiol;

$X_6$ is O or $NR_{11}$;

wherein:

each $R_1$, $R_2$, $R_3$, $R_4$, $R_5$, $R_6$, $R_8$, $R_{10}$, $R_{11}$, and Z is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;

$R_7$ is Z';

$R_9$ is —$(CH_2)_m$—$X_7$ or —$(CH_2)_m$—B, wherein
m is an integer from 1 to 8;
$X_7$ is halogen; and
B is a binding member having a binding affinity for a ligand or analyte to be detected;

(c) illuminating the biological sample with incident radiation at a wavelength to induce the SERS-active reporter molecule to produce a SERS signal; and (d) measuring the SERS signal to detect the presence or amount of one or more analytes in the biological sample.

In some embodiments, the method further comprises continuously: (a) contacting the binding member with the sample suspected of containing one or more analytes; (b) irradiating the sample with electromagnetic radiation; and (c) detecting the SERS signal. Accordingly, the detection can be carried out continuously or intermittently at predetermined times. Thus, episodic or continuous sensing of analyte(s) of interest can be performed.

1. Surface-Immobilized Target Analyte(s) of Interest

In some embodiments, the presently disclosed SERS-active nanoparticles can be used as optical tags in biological assays. In certain assays, a target molecule, e.g., an antigen, to be detected is captured by a solid surface. A binding partner, such as a ligand, e.g., an antibody, specific to the target molecule can be attached to a SERS-active nanoparticle. When contacted with the solid surface having the target molecule attached thereto, the SERS-active nanoparticle having the specific binding partner attached thereto can bind to the target molecule. The observation of a SERS signal at the solid support indicates the presence of the target molecule. Generally, the presently disclosed SERS-active nanoparticles can be conjugated to any molecule that can be used to detect the presence of a specific target molecule in an assay.

More particularly, the target analyte(s) of interest can be immobilized, for example, on a localized area of a solid support, such as a functionalized inner surface of an assay vessel, e.g., a specimen collection container. Alternatively, in a sandwich assay, the target analyte(s) of interest can be immobilized on a solid support indirectly through the binding of the analyte to a specific binding member that has been immobilized on the solid support. The immobilized target analyte(s) of interest can then be contacted with a detection reagent comprising SERS-active nanoparticles conjugated with at least one specific binding member, e.g., an antibody, having an affinity for the target analyte(s) of interest. In the sandwich assay, the immobilized specific binding member interacts with a separate surface, site, or sequence on the analyte of interest than the specific binding member that is attached to the SERS-active nanoparticle, resulting in the analyte being sandwiched between the solid support and the nanoparticle, thus generating a detectable SERS signal. In some of these embodiments, the specific binding member can be immobilized to the solid support or to the SERS-active nanoparticle through a linker, e.g., polyethylene glycol (PEG).

The SERS-active nanoparticles can interact or associate with, e.g., be reversibly or irreversibly bound to, the immobilized target analyte(s) of interest. Following a suitable incubation time, this interaction between the SERS-active nanoparticle and the immobilized target analyte(s) can be detected by illuminating the localized area of the solid support with incident radiation of the appropriate wavelength and measuring the SERS signal emitted by the SERS-active reporter molecule. Further, because each type of SERS-active reporter molecule exhibits a unique SERS spectrum, a single SERS spectrum can be used to detect a plurality of target analytes of interest by including SERS-active nanoparticles comprising different SERS-active reporter molecules in the detection reagent. Accordingly, the presently disclosed SERS-active nanoparticles can be used in multiplexed assay formats.

2. Surface-Immobilized Functionalized SERS-Active Nanoparticles

In some embodiments, the presently disclosed SERS-active nanoparticles, conjugated with a specific binding member having an affinity for the target analyte(s) of interest, can be immobilized on a localized area of a solid surface, for example, a functionalized inner surface of a specimen collection container. The immobilized SERS-active nanoparticles can be contacted with a biological sample, e.g., a blood sample, suspected of containing one or more target analyte(s) of interest. The immobilized SERS-active nanoparticles can interact or associate with, e.g., be reversibly or irreversibly bound to, the target analyte(s) of interest present in the sample. Following a suitable incubation time, this interaction between the immobilized SERS-active nanoparticle and the target analyte(s) can be detected by illuminating the localized area of the solid support with incident radiation of the proper wavelength and measuring the SERS signal emitted by the SERS-active reporter molecule. Further, because each type of SERS-active reporter molecule exhibits a unique SERS spectrum, a single SERS spectrum can be used to detect a plurality of target analytes of interest by immobilizing SERS-active nanoparticles comprising different SERS-active reporter molecules on one or more localized areas of the solid surface. The one or more localized areas of the solid surface can be illuminated with incident radiation of the appropriate wavelength and the SERS signal emitted by the SERS-active reporter molecule(s) can be measured to provide a multiplexed diagnostic assay.

3. Liquid-Based SERS Assays

In some embodiments, the presently disclosed SERS-active nanoparticles can be used in a liquid-based assay. In such assays, nanoparticles can be prepared according to known methods in the art. The nanoparticles can be solid nanoparticles, hollow nanoparticles, or encapsulated nanoparticles comprising a solid or hollow nanoparticle core and an encapsulating shell, as disclosed herein. The presently disclosed SERS-active reporter molecules can be adsorbed onto or attached, e.g., covalently attached through a chemical linker, e.g., a polyethylene glycol (PEG) linker, to the outer surface of the nanoparticle or the nanoparticle core. Binding members of a specific binding pair can be attached to an outer surface of the nanoparticle, conjugated to the reporter molecule adsorbed on or attached to the outer surface of the nanoparticle, or attached to an outer surface of the encapsulating shell. In some embodiments of the presently disclosed assays, the binding member is an antibody. The SERS-active nanoparticle having a binding member of a specific binding pair attached thereto can then be contacted with a biological sample suspected of containing one or more target analytes or ligands of interest. The specific binding member can associate, e.g., bind with, the one or more target analytes or ligands of interest.

In some liquid-based assays, a sandwich assay can be used to amplify the SERS signal as disclosed in PCT International Patent Application No. PCT/US2005/000171 to Wang et al., filed Jan. 6, 2005, which is incorporated herein by reference in its entirety. In such assays, a particular analyte is able to simultaneously bind through multiple surfaces, sites, or sequences on or within the analyte to more than one binding member, wherein the more than one binding member is attached to SERS-active nanoparticles. In those instances wherein the SERS-active nanoparticles that are simultaneously bound to the analyte through more than one binding member have attached thereto identical SERS-active dyes or SERS-active dyes exhibiting overlapping SERS spectra, the SERS signal can be amplified. It is believed that this sandwich structure or clustering of SERS-active nanoparticles around an analyte molecule generates an amplified SERS effect through an increase in the effective surface size of the clustered metallic particles, an enhancement in the electromagnetic field at the midpoint between closely spaced metallic particles, and additional local field enhancement mechanisms arising from sharp edges, kinks, or other fractal structures provided by the cluster structure.

Further, the presently disclosed dyes exhibit relatively simple Raman spectra with narrow line widths. This characteristic allows for the detection of several different Raman-active species in the same sample volume. Accordingly, this feature allows multiple SERS-active nanoparticles, each including different dyes, to be fabricated such that the Raman spectrum of each dye can be distinguished in a mixture of different types of nanoparticles. This feature allows for the multiplex detection of several different target species in a small sample volume. Thus, nanoparticles having the presently disclosed dyes associated with or attached thereto also are suitable for use in multiplexed chemical assays, in which the identity of the SERS-active nanoparticle encodes the identity of the target of the assay.

Accordingly, in some embodiments, more than one type of binding member can be attached to the nanoparticle. For example, the type of binding member attached to the nanoparticle can be varied to provide multiple reagents having different affinities for different target analytes. In this way, the assay can detect more than one analyte of interest or exhibit different selectivities or sensitivities for more than one analyte. The SERS-active nanoparticle can be tailored for samples in which the presence of one or more analytes, or the concentrations of the one or more analytes, can vary.

The presently disclosed dyes of Formula A-Y, when associated with or attached to SERS-active nanoparticles, provide spectral diversity and resolvability in multiplex assays. Each SERS-active nanoparticle, when coupled to a target-specific reagent, can encode the identity of that particular target molecule. Further, the intensity of a particular Raman signal can reveal the quantity of that particular target molecule. For example, as described hereinabove for sandwich assays, the identity of different targets captured on a solid support can be determined by using for each target SERS-active nanoparticles having different dyes of Formula A-Y associated with or attached thereto. Accordingly, the presently disclosed SERS-active nanoparticles can be used in multiplexed assays to yield qualitative and/or quantitative information regarding a target molecule without requiring position-sensitive localization of reagents.

A liquid-based SERS assay reagent can include more than one type of label, e.g., more than one type of SERS-active reporter molecule, depending on the requirements of the assay. For example, SERS-active reporter molecules exhibiting a Raman signal at different wavelengths can be used to create a unique Raman "fingerprint" for a specific analyte of interest, thereby enhancing the specificity of the assay. Different reporter molecules can be attached to different specific binding members to provide a single detection reagent capable of detecting more than one analyte of interest, e.g., a plurality of analytes of interest. Further, multiple reporter molecules can be used to create an internal reference signal that can be used to distinguish background noise from signal detection, particularly in samples that exhibit or are expected to exhibit a relatively weak signal. Additionally, more than one SERS-reporter molecule can be used to avoid or overcome non-specific radiation emitted from the sample solution under test, i.e., radiation emitted from the sample solution that cannot be attributed to direct or indirect measurement of an analyte of interest.

Further, methods for amplifying a SERS signal in a liquid-based assay, as disclosed in PCT International Patent Application No. PCT/US2008/057700 to Weidemaier et al., filed Mar. 20, 2008, which is incorporated herein by reference in its entirety, also are applicable for use with the presently disclosed SERS-active nanoparticles.

4. Magnetic Capture Liquid-Based SERS Assays

In some embodiments, the presently disclosed liquid-based SERS assay reagents can be used in a magnetic capture assay. In such embodiments, the components of the assay, including the particles, labels, and specific binding members, are introduced to a sample under test suspected of containing one or more analytes of interest. Upon allowing the reagent to interact with the complex solution, the nanoparticles can be localized using the magnetic properties of the particles. In some embodiments, a magnetic capture reagent can be used to facilitate localization of the SERS-active nanoparticles. In such embodiments, magnetic particles can be labeled with a binding member that has an affinity for one or more analytes of interest. The magnetic properties of the magnetic particles can be used to localize the SERS-active nanoparticle-analyte complex for detecting the SERS signal. Representative methods for conducting magnetic capture liquid-based SERS assays are disclosed in PCT International Patent Application No. PCT/US2008/057700 to Weidemaier et al., filed Mar. 20, 2008, which is incorporated herein by reference in its entirety. Such methods can include referencing and control methods for compensating for variations in magnetic pellet size, shape, or positioning, and methods for generating improved Raman reference spectra and spectral analysis in magnetic pull-down liquid-based assays, as also disclosed in PCT/US2008/057700.

In some embodiments, the SERS-active nanoparticle-analyte complex is localized at a predetermined area within the sample container, for example, a sample collection tube. Radiation can then be directed at the localization area and the signal can be detected. The localization of the single detection reagent can increase the reporter molecule-surface interaction and increase the signal by concentrating the SERS effect to a particular area of the sample container.

Magnetic capture of the particles can be accomplished using any method known in the art, including, but not limited to, placing a strong magnet or inducing a magnetic field at a localized area of the sample collection container.

More particularly, in some embodiments, the presently disclosed SERS-active nanoparticles, conjugated with a specific binding member having an affinity for the target analyte(s) of interest can be disposed in a specimen collection container either prior to, concurrent with, or subsequent to disposing therein a biological sample suspected of containing one or more target analytes of interest. Magnetic particles, also conjugated with a specific binding member having an affinity for the target analyte(s) of interest, can be disposed in the specimen collection container. Target analyte(s) of interest present in the sample can bind to the SERS-active nanoparticles and the magnetic particles, thereby forming a complex wherein the target analyte(s) is sandwiched between the SERS-active nanoparticle and the magnetic particle. The sandwich complexes can be concentrated in a localized area of the sample collection container by application of a magnetic field. Following a suitable incubation time, the sandwich complexes can be detected by illuminating the localized area of the sample collection container with incident radiation of the appropriate wavelength and measuring the SERS signal emitted by the SERS-active reporter molecule.

As described herein, a PEG linker can attach the specific binding member to the SERS-active nanoparticle surface to reduce non-specific binding of molecules to the nanoparticle. In some embodiments wherein a magnetic capture assay is performed, a specific binding member can be attached to the surface of a magnetic particle through a linker. In some of these embodiments, the linker molecule comprises a PEG linker. The PEG linker can vary in length, molecular weight, and functional groups useful for linking the specific binding member to the magnetic particle, as described herein.

In some embodiments, the PEG molecule or PEG-specific binding member conjugate is attached to the magnetic particle through the reaction of thiol-reactive maleimide groups on the PEG molecule with thiol groups on the magnetic particle surface to form a carbon-sulfur bond. The surface of the magnetic particle can be functionalized with a thiol group by treating a carboxylated magnetic particle with an amine-terminated molecule containing an internal disulfide. The disulfide can be cleaved with dithiothreitol or other suitable agent, exposing a reactive thiol group. In some of these embodiments, the PEG linker comprises a heterobifunctional PEG linker with an amine-reactive N-hydroxysuccinimide-ester on one end and a maleimide group on the other end.

5. Representative Target Analytes of Interest

The presently disclosed methods can be used to assess or measure the presence or amount of one or more target analytes in a biological sample. The term "analyte," as used herein, generally refers to a substance to be detected, which can be present or suspected of being present in a test sample. More particularly, an "analyte" can be any substance for which there exists a naturally occurring specific binder partner, such as a binding protein or receptor, or for which a specific binding partner can be prepared. Accordingly, an "analyte" is a substance that can bind one or more specific binding partners in an assay. In some embodiments, the analyte can be any compound, such as a metabolite, to be detected or measured and which has at least one binding site.

The target analytes can be any molecule or compound, of which the presence or amount is to be determined in a sample under test. Examples of classes of analytes that can be measured by the presently disclosed methods include, but are not limited to amino acids, peptides, polypeptides, proteins, carbohydrates, fatty acid, lipids, nucleotides, oligonucleotides, polynucleotides, glycoproteins, such as prostate specific antigen (PSA), proteoglycans, lipoproteins, lipopolysaccharides, drugs, drug metabolites, small organic molecules, inorganic molecules and natural or synthetic polymers. Examples of target analytes include, but are not limited to, glucose, free fatty acids, lactic acid, C-reactive protein and anti-inflammatory mediators, such as cytokines, eicosanoids, or leukotrienes. In some embodiments, the target analytes are selected from the group consisting of fatty acids, C-reactive protein, and leukotrienes. In another embodiment, the target analytes are selected from the group consisting of glucose, lactic acid and fatty acids.

More particularly, in some embodiments, the analyte can include glucose, as described hereinabove, prostate specific antigen (PSA), creatine kinase MB (CKMB) isoenzyme, cardiac troponin I (cTnI) protein, thyroid-stimulating hormone (TSH), influenza A (Flu A) antigen, influenza B (Flu B) antigen, and respiratory syncytial virus (RSV) antigen.

Prostate specific antigen (PSA) is a protein produced by the cells of the prostate gland and typically is present in small quantities in the serum of normal men. PSA can be elevated in men afflicted with prostate cancer or other prostate disorders. Normal PSA blood levels typically are considered to be between about 0.0 and 4.0 ng/mL, whereas PSA levels between 4 and 10 ng/mL (nanograms per milliliter) are considered suspicious.

Creatine kinase (CK), also known as phosphocreatine kinase or creatine phosphokinase (CPK) is an enzyme found predominately in the heart, brain, and skeletal muscle. Creatine kinase comprises three isoenzymes that differ slightly in structure: CK-BB (also referred to as CPK-1) is concentrated in the brain and lungs; CK-MB (also referred to as CPK-2) is found mostly in the heart; and CK-MM (also referred to as CPK-3) is found mostly in skeletal muscle. Diagnostic tests for specific CPK isoenzymes typically are performed when the total CPK level is elevated and can help differentiate the source of the damaged tissue. For example, an injury to the brain, e.g., a stroke, or lungs, e.g., a pulmonary embolism, can be associated with elevated levels of CK-BB. Further, CK-MM is normally responsible for almost all CPK enzyme activity in healthy subjects. When this particular isoenzyme is elevated, it usually indicates injury or stress to skeletal muscle.

CK-MB levels can be measured in subjects who have chest pain to diagnose whether they had a heart attack and/or as an as an indication for myocardial damage during heart attacks. Typically, CK-MB values exhibit a significant rise in CK-MB values in the first two to three hours after a heart attack. If there is no further damage to the heart muscle, the level peaks at 12-24 hours and returns to normal 12-48 hours after tissue death. CK-MB levels do not usually rise with chest pain caused by angina, pulmonary embolism (blood clot in the lung), or congestive heart failure. Elevated CK-MB levels also can be observed in subjects suffering from myocarditis (inflammation of the heart muscle, for example, due to a virus), electrical injuries, trauma to the heart, heart defibrillation, and open heart surgery. Blood serum CK-MB values measured in such assays typically range from about 0.0 to about 10 ng/mL. CK-MB values greater than about 5 ng/mL typically confirm a diagnosis of myocardial infarction.

Cardiac troponin I (cTnI) protein also is an independent predictor of major cardiac events. See, e.g., Polancyzk, C. A., et al., "Cardiac troponin I as a predictor of major cardiac events in emergency department patients with acute chest pain," *J. Am. Coll. Cardiol.*, 32, 8-14 (1998). cTnI values in blood serum measured in subject suspected of having a myocardial infarction range from about 0.4 ng/mL to about 1.5 ng/mL. Id. cTnI assays with lower detection limits of 0.1 ng/mL have the potential, however, to be more sensitive for detecting myocardial injury. Id.

Thyroid-stimulating hormone (TSH) is synthesized and secreted by thyrotrope cells in the anterior pituitary gland which regulates the endocrine function of the thyroid gland. TSH levels are tested in the blood of subjects suspected of suffering from an excess (hyperthyroidism) or deficiency (hypothyroidism) of thyroid hormone. Normal TSH levels in adults range from about 0.4 milli-international units per liter (mIU/L) to about 4.5 mIU/L. Current assays for TSH include sandwich ELISA for the measurement of TSH in blood serum or plasma, in which TSH in the sample is bound by anti-TSH monoclonal antibodies and then detected by spectrophotometry or colorimetry.

The presently disclosed assays also can be used to detect influenza viruses. Three types of influenza viruses exist: Influenzavirus A; Influenzavirus B; and Influenzavirus C. Influenza A (Flu A) and Influenza C (Flu C) infect multiple species, while Influenza B (Flu B) infects almost exclusively humans. Type A viruses are the most virulent human pathogens among the three influenza types and typically cause the most severe disease. Influenza A virus can be subdivided into different serotypes based on the antibody response to these viruses and include H1N1 (i.e., "Spanish Flu"); H2N2 (i.e., "Hong Kong Flu"); H5N1 (i.e., avian influenza strain or "Bird Flu"); H7N7; H1N2; H9N2; H7N2; H7N3, and H10N7. Influenza B is almost exclusively a human pathogen and is less common than Influenza A and only includes one serotype. The influenza C virus infects humans and pigs and can cause severe illness and local epidemics, but is less common than the other types.

Diagnostic tests available for influenza include rapid immunoassay, immunofluorescence assay, polymerase chain reaction (PCR), serology, and viral culture. Immunofluorescence assays entail staining of specimens immobilized on microscope slides using fluorescent-labeled antibodies for observation by fluorescence microscopy. Culture methods employ initial viral isolation in cell culture, followed by hemadsorption inhibition, immunofluorescence, or neutralization assays to confirm the presence of the influenza virus. Antigen detection assays to diagnose influenza infection include DIRECTIGEN™ EZ Flu A or DIRECTIGEN™ EZ Flu A+B test kits, (available from BD Diagnostic Systems, Sparks, Md.). Such rapid chromatographic immunoassays can be used for the direct detection of influenza A or influenza A and B viral antigens from nasopharyngeal washes/aspirates, nasopharyngeal swabs and throat swabs of symptomatic patients. Further, such diagnostic tests can be used to distinguish between influenza A and influenza B.

Respiratory syncytial virus (RSV) is the most common cause of bronchiolitis and pneumonia among infants and children under 1 year of age. RSV is a negative-sense, enveloped RNA virus. Diagnosis of RSV infection can be made by virus isolation, detection of viral antigens, detection of viral RNA, demonstration of a rise in serum antibodies, or a combination of these approaches. Traditional methods for detection of respiratory viruses have included cell culture and direct fluorescent antibody (DFA). Enzyme immunoassay (EIA) and rapid manual systems are available for specific viruses such as Influenza A/B and RSV. Currently, most clinical laboratories use antigen detection assays to diagnose RSV infection, such as DIRECTIGEN™ EZ RSV test (available from BD Diagnostic Systems, Sparks, Md.), which is a rapid chromatographic immunoassay for the direct and qualitative detection of RSV antigen in nasopharyngeal washes, nasopharyngeal aspirates, nasopharyngeal swabs and nasopharyngeal swab/washes from subjects suspected of having a viral respiratory infection.

Accordingly, in some embodiments, the presently disclosed subject matter provides a method for detecting the presence or amount of a target analyte in a biological sample, e.g., blood serum, wherein the target analyte includes glucose, prostate specific antigen (PSA), creatine kinase MB (CKMB) isoenzyme, cardiac troponin I (cTnI) protein, thyroid-stimulating hormone (TSH), influenza A (Flu A) antigen, influenza B (Flu B) antigen, and respiratory syncytial virus (RSV) antigen, the method comprising contacting the biological sample with a reagent comprising one or more SERS-active nanoparticles having associated therewith at least one specific binding member having an affinity for the analyte, e.g., a specific binding protein or monoclonal or polyclonal antibody for the analyte of interest, and at least one SERS-active reporter molecule of Formula A-Y; illuminating the biological sample with incident radiation at a wavelength to induce the SERS-active reporter molecule to produce a SERS signal; and measuring the SERS signal to detect the presence or amount of analyte in the biological sample.

As used herein, the term "carbohydrate" includes, but is not limited to monosaccharides, disaccharides, oligosaccharides and polysaccharides. "Carbohydrate" also includes, but is not limited to, molecules comprising carbon, hydrogen and oxygen that do not fall within the traditional definition of a saccharide, i.e., an aldehyde or ketone derivative of a straight chain polyhydroxyl alcohol, containing at least three carbon atoms. Thus, for example, a carbohydrate as used herein can contain fewer than three carbon atoms.

The term "fatty acids," as used herein include all fatty acids, including free fatty acids (FFA) and fatty acids esterified to other molecules. Examples of specific fatty acids include, but are not limited to, palmitate, stearate, oleate, linoleate, linolenate, and arachidonate. The term "free fatty acid" is used herein as it is known in the art in that FFA are not part of other molecules, such as triglycerides or phospholipids. Free fatty acids also include non-esterified fatty acids that are bound to or adsorbed onto albumin. As used herein, the term "unbound free fatty acid" (unbound FFA) is used to denote a free fatty acid or free fatty acids that are not bound or adsorbed onto albumin or other serum proteins.

As used herein, the term "lipid" is used as it is in the art, i.e., a substance of biological origin that is made up primarily or exclusively of nonpolar chemical groups such that it is readily soluble in most organic solvents, but only sparingly soluble in aqueous solvents. Examples of lipids include, but are not limited to, fatty acids, triacylglycerols, glycerophospholipids, sphingolipids, cholesterol, steroids and derivatives thereof. For example, "lipids" include but are not limited to, the ceramides, which are derivatives of sphingolipids and derivatives of ceramides, such as sphingomyelins, cerebrosides and gangliosides. "Lipids" also include, but are not limited to, the common classes of glycerophospholipds (or phospholipids), such as phosphatidic acid, phosphatidylethanolamine, phosphatidylcholine, phosphatidylserine, phosphatidylinositol, phosphatidylglycerol, and the like.

As used herein, a "drug" can be a known drug or a drug candidate, whose activity or effects on a particular cell type are not yet known. A "drug metabolite" is any of the by-products or the breakdown products of a drug that is changed chemically into another compound or compounds. As used herein, "small organic molecule" includes, but is not limited to, an organic molecule or compound that does not fit precisely into other classifications highlighted herein. More particularly, the term "small organic molecule" as used herein, refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds.

Further, in some embodiments, the presently disclosed subject matter provides a method of detecting one or more of a nucleic acid, e.g., deoxyribonucleic acid (DNA), a DNA fragment, a nucleotide, a polynucleotide, an oligonucleotide, and the like. Generally, the method comprises contacting one or more of a nucleic acid, a DNA fragment, a nucleotide, a polynucleotide, an oligonucleotide, with a presently disclosed SERS-active nanoparticle having an oligonucleotide attached thereto and detecting the presence of or a change in the SERS spectrum thereof. In exemplary embodiments, the oligonucleotides attached to the presently disclosed SERS active nanoparticles have a sequence, or sequences, complementary to portions of the sequence of the target nucleic acid, DNA fragment, nucleotide, polynucleotide, or oligonucleotide. A detectable SERS spectrum, and/or a change in the SERS spectrum, can be observed as a result of the hybridization of the oligonucleotide attached to the SERS active nanoparticle and the target nucleic acid, DNA fragment, nucleotide, polynucleotide, or oligonucleotide.

The presently disclosed SERS-active nanoparticles, the oligonucleotides, or both can be functionalized to attach the oligonucleotides to the nanoparticles. Such methods are known in the art. For example, oligonucleotides functionalized with alkanethiols at the 3'-termini or 5'-termini readily attach to nanoparticles, including gold and other metal nanoparticles. See, e.g., Whitesides, *Proceedings of the Robert A. Welch Foundation* 39th *Conference On Chemical Research Nanophase Chemistry*, Houston, Tex., pp. 109-121 (1996); see also, Mucic et al., *Chem. Commun.* 555-557 (1996) (describing a method of attaching 3' thiol DNA to flat gold surfaces which also can be used to attach oligonucleotides to nanoparticles).

Other functional groups suitable for attaching oligonucleotides to solid surfaces include phosphorothioate groups (see, e.g., U.S. Pat. No. 5,472,881 to Beebe et al., which is incorporated herein by reference in its entirety, for the binding of oligonucleotide-phosphorothioates to gold surfaces), substituted alkylsiloxanes (see, e.g., Burwell, *Chemical Technology*, 4, 370-377 (1974) and Matteucci and Caruthers, *J. Am. Chem. Soc.*, 103, 3185-3191 (1981) for binding of oligonucleotides to silica and glass surfaces, and Grabar et al., *Anal. Chem.*, 67, 735-743 (1995) for binding of aminoalkylsiloxanes and for similar binding of mercaptoaklylsiloxanes). Oligonucleotides terminated with a 5' thionucleoside or a 3' thionucleoside also can be used for attaching oligonucleotides to solid surfaces.

Other methods are known in the art for attaching oligonucleotides to nanoparticles. Such methods are described in the following representative references. Nuzzo et al., *J. Am. Chem. Soc.*, 109, 2358 (1987) (disulfides on gold); Allara and Nuzzo, *Langmuir*, 1, 45 (1985) (carboxylic acids on aluminum); Allara and Tompkins, *J. Colloid Interface Sci.*, 49, 410-421 (1974) (carboxylic acids on copper); Iler, *The Chemistry Of Silica*, Chapter 6, John Wiley & Sons, New York (1979) (carboxylic acids on silica); Timmons and Zisman, *J. Phys. Chem.*, 69, 984-990 (1965) (carboxylic acids on platinum); Soriaga and Hubbard, *J. Am. Chem. Soc.*, 104, 3937 (1982) (aromatic ring compounds on platinum); Hubbard, *Acc. Chem. Res.*, 13, 177 (1980) (sulfolanes, sulfoxides and other functionalized solvents on platinum); Hickman et al., *J. Am. Chem. Soc.*, 111, 7271 (1989) (isonitriles on platinum); Maoz and Sagiv, *Langmuir*, 3, 1045 (1987) (silanes on silica); Maoz and Sagiv, *Langmuir*, 3, 1034 (1987) (silanes on silica); Wasserman et al., *Langmuir*, 5, 1074 (1989) (silanes on silica); Eltekova and Eltekov, *Langmuir*, 3, 951 (1987) (aromatic carboxylic acids, aldehydes, alcohols and methoxy groups on titanium dioxide and silica); Lec et al., *J. Phys. Chem.*, 92, 2597 (1988) (rigid phosphates on metals).

Further, oligonucleotides functionalized with a cyclic disulfide, for example, cyclic disulfides having a 5- to 6-membered ring including at least two sulfur atoms, also are suitable for use with the presently disclosed subject matter. Suitable cyclic disulfides are available commercially or can be synthesized by known procedures. The reduced form of the cyclic disulfides also can be used. In some embodiments, the cyclic disulfide can further have a linker, for example, a hydrocarbon moiety, such as a steroid residue, attached thereto.

In some embodiments, polynucleotides (e.g., oligonucleotides) are attached to the outer surface of a SERS-active nanoparticle through a linker molecule. In particular embodiments, the linker molecule comprises a PEG linker. The PEG linker can be attached to the polynucleotide and the nanoparticle through any suitable method, including those described elsewhere herein.

Each nanoparticle can have a plurality of oligonucleotides attached thereto. As a result, each nanoparticle-oligonucleotide conjugate can bind to a plurality of oligonucleotides or nucleic acids having a complementary sequence. Methods of making oligonucleotides of a predetermined sequence are well-known. See, e.g., Sambrook et al., *Molecular Cloning: A Laboratory Manual* (2nd ed. 1989) and F. Eckstein (ed.) *Oligonucleotides and Analogues*, 1st Ed. (Oxford University Press, New York, 1991). Solid-phase synthesis methods can be used for oligoribonucleotides and oligodeoxyribonucleotides (known methods of synthesizing DNA also are useful for synthesizing RNA). Oligoribonucleotides and oligodeoxyribonucleotides also can be prepared enzymatically.

Accordingly, the presently disclosed subject matter provides a method for detecting nucleic acids. Any type of nucleic acid can be detected by the presently disclosed method. Therefore, the presently disclosed methods can be used in several applications where the detection of a nucleic acid is required, for example, in the diagnosis of disease and in sequencing of nucleic acids. Examples of nucleic acids that can be detected by the presently disclosed methods include, but are not limited to, genes (e.g., a gene associated with a particular disease), viral RNA and DNA, bacterial DNA, fungal DNA, cDNA, mRNA, RNA and DNA fragments, oligonucleotides, synthetic oligonucleotides, modified oligonucleotides, single-stranded and double-stranded nucleic acids, natural and synthetic nucleic acids, and the like.

Representative examples of the uses of the methods of detecting nucleic acids include, but are not limited to, the diagnosis and/or monitoring of viral diseases (e.g., human immunodeficiency virus, hepatitis viruses, herpes viruses, cytomegalovirus, and Epstein-Barr virus), bacterial diseases (e.g., tuberculosis, Lyme disease, *H. pylori, Escherichia coli* infections, *Legionella* infections, *Mycoplasma* infections, *Salmonella* infections), sexually transmitted diseases (e.g., gonorrhea), inherited disorders (e.g., cystic fibrosis, Duchenne muscular dystrophy, phenylketonuria, sickle cell anemia), and cancers (e.g., genes associated with the development of cancer); in forensics; in DNA sequencing; for paternity testing; for cell line authentication; for monitoring gene therapy; and for many other purposes.

The nucleic acid to be detected can be isolated by known methods, or can be detected directly in cells, tissue samples, biological fluids (e.g., saliva, urine, blood, serum, and the like), solutions containing PCR components, solutions containing large excesses of oligonucleotides or high molecular weight DNA, and other samples, as also known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995). Methods of preparing nucleic acids for detection with hybridizing probes also are well known in the art. See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995). If a nucleic acid is present in small amounts, it can be applied by methods known in the art, including polymerase chain reaction (PCR) amplification.

See, e.g., Sambrook et al., *Molecular Cloning: A Laboratory Manual* (2nd ed. 1989) and B. D. Hames and S. J. Higgins, Eds., *Gene Probes* 1 (IRL Press, New York, 1995).

One presently disclosed method for detecting nucleic acid comprises contacting a nucleic acid with one or more of the presently disclosed nanoparticles having oligonucleotides attached thereto. The nucleic acid to be detected can have at least two portions. The lengths of these portions and the distance(s), if any, between them are chosen so that when the oligonucleotides on the nanoparticles hybridize to the nucleic acid, a detectable SERS signal can be observed. These lengths and distances can be determined empirically and depend on the type of particle used and its size and the type of electrolyte present in solutions used in the assay (as is known in the art, certain electrolytes affect the conformation of nucleic acids).

Also, when a nucleic acid is to be detected in the presence of other nucleic acids, the portions of the nucleic acid to which the oligonucleotides on the nanoparticles are to bind must be chosen so that they contain sufficient unique sequence so that detection of the nucleic acid will be specific. Guidelines for doing so are well known in the art. The contacting of the nanoparticle-oligonucleotide conjugates with the nucleic acid takes place under conditions effective for hybridization of the oligonucleotides on the nanoparticles with the target sequence(s) of the nucleic acid. These hybridization conditions are well known in the art and can readily be optimized for the particular system employed. See, e.g., Sambrook et al., *Molecular Cloning: A Laboratory Manual* (2nd ed. 1989). In some embodiments, stringent hybridization conditions are employed.

Representative methods for detecting nucleic acids by using SERS-active nanoparticles having oligonucleotides attached thereto are disclosed in U.S. Pat. No. 7,169,556 to Park et al., which is incorporated herein by reference in its entirety.

6. Representative Instrumentation for Detecting a SERS Signal Emitted by a Sample Under Test In some embodiments, a laser serves as the excitation source of the incident radiation used to detect one or more target analytes of interest. One of ordinary skill in the art upon review of the presently disclosed subject matter could ascertain the type of laser, including the strength and excitation wavelength, suitable for use with the SERS-active reporter molecules described herein. Radiation scattered or emitted from the sample can be detected using detection systems known in the art.

In some embodiments, more than one type of radiation source, or more than one excitation wavelength, can be used. For example, in embodiments wherein two analytes of interest are to be detected, the single detection reagent can include two distinct types of SERS-active reporter molecules and/or two distinct types of specific binding members. Accordingly, incident radiation of different wavelengths can be used to produce distinct Raman signals for each analyte of interest. As one of ordinary skill in the art would recognize upon review of the presently disclosed subject matter, the selection of the particular wavelength(s) to be used depends on the analyte of interest, the specific binding members used, and the particular SERS-active reporter molecules used.

The presently disclosed assay can be conducted with any suitable Raman spectrometer systems known in the art, including, for example, a Multimode Multiple Spectrometer Raman Spectrometer (Centice, Morrisville, N.C., United States of America), such as the Raman spectrometer system disclosed in U.S. Pat. No. 7,002,679 to Brady et al., which is incorporated herein by reference in its entirety. Additional instrumentation suitable for use with the presently disclosed SERS-active nanoparticles is disclosed in PCT International Patent Application No. PCT/US2008/057700 to Weidemaier et al., filed Mar. 20, 2008, which is incorporated herein by reference in its entirety.

Sensing devices, such as optical detectors, radiation sources, and computer systems, microprocessors, and computer software and algorithms, can be used in any combination in practicing the methods disclosed herein. Accordingly, in some embodiments, software, or other computer readable instructions can be used to interpret, analyze, compile, or otherwise parse output data related to the presently disclosed optical assay. The software or other computer system can be used to display, store, or transmit output data, whether in digital or other forms to one or more users.

7. Sample Collection Container

In some embodiments, the sample container is selected from the group consisting of a cuvette, a tube, such as a blood collection tube, or any other sample collection container compatible with the sample under test and SERS measurements. In some embodiments, the sample collection container, e.g., a tube, can have an internal pressure that is less than the atmospheric pressure of the surrounding environment. Such sample collection containers are disclosed in U.S. Pat. Nos. 5,860,937 to Cohen; 5,906,744 to Carroll et al.; and 6,821, 789 to Augello et al., each of which is incorporated herein by reference in their entirety. Additional assay vessels suitable for use with the presently disclosed SERS-active nanoparticles, in particular for use in magnetic capture assays, are disclosed in PCT International Patent Application No. PCT/US2008/057700 to Weidemaier et al., filed Mar. 20, 2008, which is incorporated herein by reference in its entirety. Further, in some embodiments, the sample collection container includes a single detection reagent comprising the presently disclosed SERS-active nanoparticles. In such embodiments, the sample collection container has a single detection reagent disposed therein before the user, e.g., a patient or a medical technician, collects the biological sample, e.g., blood, to be detected. The single detection reagent, for example, can be immobilized on an inner surface, e.g., an inner wall, of the sample collection container or simply otherwise disposed within the sample container.

The sample collection container, for example, a blood collection tube, can be shipped to the user with the single detection reagent disposed therein. Alternatively, the user can select a suitable detection reagent and introduce the detection reagent into the collection device before collecting the sample specimen. Further, the presently disclosed subject matter can include a kit comprising one or more of a sample collection container, such as a blood collection tube, one or more reagents, such as one or more single detection reagents comprising nanoparticles having a SERS-active reporter molecule attached thereto, magnetic capture particles, and individual components thereof. Such kits can include any number of the components of the assay, including, but not limited to, multiple reporter molecules or multiple specific binding members either attached to a nanoparticle or packaged separately therefrom.

As used herein, the term "sample" includes any liquid or fluid sample, including a sample derived from a biological source, such as a physiological fluid, including whole blood or whole blood components, such as red blood cells, white blood cells, platelets, serum and plasma; ascites; urine; saliva; sweat; milk; synovial fluid; peritoneal fluid; amniotic fluid; percerebrospinal fluid; lymph fluid; lung embolism; cerebrospinal fluid; pericardial fluid; cervicovaginal samples; tissue extracts; cell extracts; and other constituents of the body that are suspected of containing the analyte of interest. In addition to physiological fluids, other liquid samples, such as water, food products and the like, for the performance of environmental or food production assays are suitable for use with the presently disclosed subject matter. A solid material suspected of containing the analyte also can be used as the test sample. In some instances it might be beneficial to modify a solid test sample to form a liquid medium or to release the analyte.

In some embodiments, the sample can be pre-treated prior to use, such as preparing plasma from blood, diluting viscous fluids, or the like. Such methods of treatment can involve filtration, distillation, concentration, inactivation of interfering compounds, and the addition of reagents.

The sample can be any sample obtained from a subject. The term "subject" refers to an organism, tissue, or cell from which a sample can be obtained. A subject can include a human subject for medical purposes, such as diagnosis and/or treatment of a condition or disease, or an animal subject for medical, veterinary purposes, or developmental purposes. A subject also can include sample material from tissue culture, cell culture, organ replication, stem cell production and the like. Suitable animal subjects include mammals and avians. The term "avian" as used herein includes, but is not limited to, chickens, ducks, geese, quail, turkeys, and pheasants. The term "mammal" as used herein includes, but is not limited to, primates, e.g, humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. Preferably, the subject is a mammal or a mammalian cell. More preferably, the subject is a human or a human cell. Human subjects include, but are not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. A subject also can refer to cells or collections of cells in laboratory or bioprocessing culture in tests for viability, differentiation, marker production, expression, and the like.

The presently disclosed methods can be used to diagnose, for the prognosis, or the monitoring of a disease state or condition. As used herein, the term "diagnosis" refers to a predictive process in which the presence, absence, severity or course of treatment of a disease, disorder or other medical condition is assessed. For purposes herein, diagnosis also includes predictive processes for determining the outcome resulting from a treatment. Likewise, the term "diagnosing," refers to the determination of whether a sample specimen exhibits one or more characteristics of a condition or disease. The term "diagnosing" includes establishing the presence or absence of, for example, a target antigen or reagent bound targets, or establishing, or otherwise determining one or more characteristics of a condition or disease, including type, grade, stage, or similar conditions. As used herein, the term "diagnosing" can include distinguishing one form of a disease from another. The term "diagnosing" encompasses the initial diagnosis or detection, prognosis, and monitoring of a condition or disease.

The term "prognosis," and derivations thereof, refers to the determination or prediction of the course of a disease or condition. The course of a disease or condition can be determined, for example, based on life expectancy or quality of life. "Prognosis" includes the determination of the time course of a disease or condition, with or without a treatment or treatments. In the instance where treatment(s) are contemplated, the prognosis includes determining the efficacy of a treatment for a disease or condition.

As used herein, the term "risk" refers to a predictive process in which the probability of a particular outcome is assessed.

The term "monitoring," such as in "monitoring the course of a disease or condition," refers to the ongoing diagnosis of samples obtained from a subject having or suspected of having a disease or condition.

The term "marker" refers to a molecule, such as a protein, including an antigen, that when detected in a sample is characteristic of or indicates the presence of a disease or condition.

The presently disclosed subject matter also provides methods for monitoring disease states in a subject, including chronic diseases, such as, but not limited to, heart disease, coronary artery disease, diabetes, metabolic disorders, inflammatory diseases, such as rheumatoid arthritis, and cancer. The metabolic disorders can include, but are not limited to, hyperlipidemia, hypolipidemia, hyperthyroidism, and hypothyroidism.

Further, the presently disclosed methods can be used to monitor specific markers of a chronic disease. By monitoring the concentrations of molecular artifacts, metabolites, and deleterious and/or beneficial molecules of a disease state, the subject's progression, regression or stability can be assessed, and treatments can, in turn be adjusted or revised accordingly. For example, markers for heart disease that could be monitored in vivo using the presently disclosed biosensors include, but are not limited to, total fatty acids, lactate, glucose, free fatty acids and various cardiotonic agents, such as, but not limited to cardioglycosides and sympathomimetics. Markers of diabetes include, but are not limited to, glucose, lactate and fatty acids. Likewise, markers for coronary artery disease include, but are not limited to, C-reactive peptide and free fatty acids. Generally, markers of various metabolic disorders include, but are not limited to, specific fatty acids.

The presently disclosed SERS-active nanoparticles also are suitable for use in devices for monitoring drug treatment. Indeed, the SERS-active nanoparticle can be designed to specifically bind a drug, drug candidate or a drug metabolite. In this manner, the plasma concentration of the drug could be monitored and dosages could be adjusted or maintained based on the concentration measurements provided by the SERS method. Accordingly, a pharmaceutical regimen could be individualized for a particular subject, including the use of a SERS-active nanoparticle that can specifically and reversibly bind the drug or drug metabolite to determine plasma concentrations of the drug. The concentrations provided by the SERS method can then be used to determine the bioavailability of the drug in the subject. The dose of the drug administered to the subject can then be altered to increase or decrease the bioavailability of the drug to the subject to provide maximum therapeutic benefits and avoiding toxicity.

The presently disclosed SERS-active nanoparticles also can be used to simultaneously monitor a variety of metabolites, the measurements of which could be used to profile the subject's metabolic or physical state. For example, during extended periods of strenuous exercise, glucose is broken down in anaerobic processes to lactic acid. The presently disclosed SERS-active nanoparticles can be used to determine lactate thresholds of athletes, to maximize the benefits of training and decrease recovery time. Similarly, the SERS-active nanoparticles can be used to determine lactate thresholds in soldiers to prevent fatigue and exhaustion and to decrease recovery time. To that end, the presently disclosed SERS-active nanoparticles can be used to monitor glucose levels, lactic acids levels and other metabolites during exercise or physical stress.

The presently disclosed SERS-active nanoparticles also can be used to monitor a condition or disease state in a patient in an acute care facility, such as an emergency room or a post-operative recovery room or a hospital. For example, in embodiments providing a method for monitoring glucose levels in a subject, studies have shown that mortality can be decreased by as much as 30% in post-operative patients when glucose levels are monitored and kept normal. Thus, the presently disclosed SERS-based diagnostic assays can be used in situations where monitoring glucose or other metabolites is essential to recovery or the overall health of the subject.

The amount of one or more analytes present in a sample under test can be represented as a concentration. As used herein, the term "concentration" has its ordinary meaning in the art. The concentration can be expressed as a qualitative value, for example, as a negative- or positive-type result, e.g., a "YES" or "NO" response, indicating the presence or absence of a target analyte, or as a quantitative value. Further, the concentration of a given analyte can be reported as a relative quantity or an absolute quantity, e.g., as a "quantitative value." The presently disclosed assays, in some embodiments, are capable of detecting an analyte of interest at a concentration range of about 5 fg/mL to about 500 ng/mL; in some embodiments, at a concentration range of about 10 fg/mL to about 100 ng/mL; in some embodiments, at a concentration range of about 50 fg/mL to about 50 ng/mL.

The quantity (concentration) of an analyte can be equal to zero, indicating the absence of the particular analyte sought or that the concentration of the particular analyte is below the detection limits of the assay. The quantity measured can be the SERS signal without any additional measurements or manipulations. Alternatively, the quantity measured can be expressed as a difference, percentage or ratio of the measured value of the particular analyte to a measured value of another compound including, but not limited to, a standard or another analyte. The difference can be negative, indicating a decrease in the amount of measured analyte(s). The quantities also can be expressed as a difference or ratio of the analyte(s) to itself, measured at a different point in time. The quantities of analytes can be determined directly from a generated signal, or the generated signal can be used in an algorithm, with the algorithm designed to correlate the value of the generated signals to the quantity of analyte(s) in the sample.

The presently disclosed SERS-active nanoparticles are amenable for use with devices capable of continuously measuring the concentrations of one or more analytes. As used herein, the term "continuously," in conjunction with the measuring of an analyte, is used to mean the device either generates or is capable of generating a detectable signal at any time during the life span of the device. The detectable signal can be constant, in that the device is always generating a signal, even if a signal is not detected. Alternatively, the device can be used episodically, such that a detectable signal can be generated, and detected, at any desired time.

B. Cellular Imaging

The small size of the presently disclosed SERS-active nanoparticles allow the nanoparticles to be incorporated into cells. For example, the use of SERS to study the complexation of a chemotherapeutic agent with DNA has been demonstrated. See Nabiev, I. R., et al., "Selective analysis of antitumor drug interactions with living cancer cells as probed by surface-enhanced Raman spectroscopy, $Eur.$ $Biophys.$ $J.,$ 19, 311-316 (1991); Morjani, H. et al., "Molecular and cellular interactions between intoplicine, DNA, and topoisomerase II studied by surface-enhanced Raman scattering spectroscopy," $Cancer$ $Res.,$ 53, 4784-4790 (1993). SERS also has been used to investigate the mechanism of chemotherapeutic resistance to certain cancers. See Breuzard, G., et al., "Surface-enhanced Raman scattering reveals adsorption of mitoxantrone on plasma membrane of living cells," $Biochem.$ $Biophys.$ $Res.$ $Comm.,$ 320, 615-621 (2004). Further, SERS has been used to characterize the distribution of particular chemicals within cells and to distinguish between the cytoplasm and the nucleus of the cell. See Kneipp, K., et al., "Surface-enhanced Raman spectroscopy in single living cells using gold nanoparticles," $Appl.$ $Spectrosc.,$ 56(2), 150-154 (2002).

Accordingly, in some embodiments, nanoparticles labeled with the presently disclosed dyes can be used for cellular imaging, for example, to distinguish between abnormal cells, for example, a cell exhibiting an anomaly, such as a cancerous cell, versus normal cells in a biological sample. In such embodiments, the intensity of the Raman signal arising from the dye is proportional to the density of cells detected. Further, in some embodiments, the nanoparticles labeled with the presently disclosed dyes also can be labeled with another species, such as a specific binding member of a binding pair, for example, an antibody, to facilitate binding to a cell of interest. The use of SERS-active nanoparticles for cellular imaging is described in U.S. Patent Application Publication Nos. 2006/0054506 and 2006/0046313, each of which is incorporated herein by reference in its entirety.

Accordingly, in some embodiments, the presently disclosed subject matter provides a method for detecting the presence of one or more target structures in a sample cell, the method comprising:

(a) contacting one or more sample cells with one or more SERS-active nanoparticles labeled with one or more binding members under conditions suitable for binding of the one or more binding members to one or more target structures in the sample cell, wherein the SERS-active nanoparticle has associated therewith a dye of Formula A-Y capable of producing a distinguishable Raman signal:

A-Y wherein:

A is selected from the group consisting of:

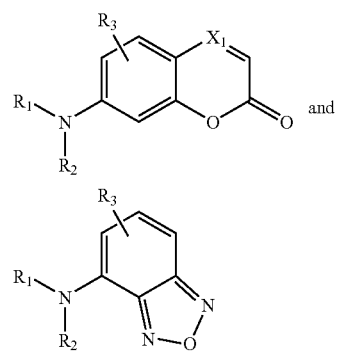

wherein $X_1$ is $CR_4$ or N;

Y is selected from the group consisting of:

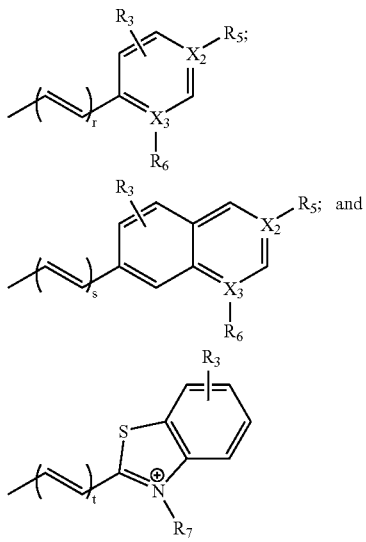

wherein:
r, s, and t are each independently an integer from 1 to 8;
each $X_2$ and $X_3$ is independently selected from the group consisting of C, S, and N, under the proviso that (i) when $X_2$ is C or S, $R_5$ is Z, or when $X_3$ is C or S, $R_6$ is Z, as Z is defined herein below; (ii) if both $X_2$ and $X_3$ are N at the same time, at least one of $R_5$ and $R_6$ is absent; and (iii) when $X_2$ is N, $R_5$ when present is Z', or when $X_3$ is N, $R_6$ when present is Z', wherein Z' is selected from the group consisting of:

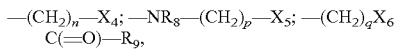

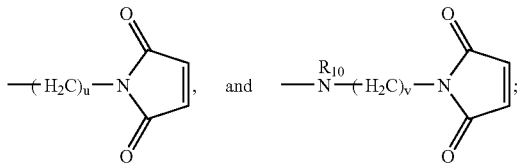

wherein:
n, p, q, u, and v are each independently an integer from 1 to 8;
$X_4$ and $X_5$ are each independently selected from the group consisting of hydroxyl, amino, and thiol;
$X_6$ is O or $NR_{11}$;
wherein:
each $R_1$, $R_2$, $R_3$, $R_4$, $R_5$, $R_6$, $R_8$, $R_{10}$, $R_{11}$, and Z is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl;
$R_7$ is Z';
$R_9$ is $-(CH_2)_m-X_7$ or $-(CH_2)_m-B$, wherein m is an integer from 1 to 8;
$X_7$ is halogen; and
B is a binding member having a binding affinity for a ligand or analyte to be detected; and
(b) detecting one or more distinguishable SERS signals from the sample cell to indicate the presence of the one or more target structures in the sample cell.

In some embodiments, the method further comprises contacting the one or more SERS-active nanoparticles with one or more reference cells. In some embodiments, the method further comprises analyzing the one of more distinguishable SERS signals detected from the sample cell to construct a profile of the one or more target structures in the sample cell. In some embodiments, the method further comprises analyzing the one or more distinguishable SERS signals detected from the reference cell to construct a profile of the one or more target structures in the reference cell. In some embodiments, the method further comprises comparing the profile of the one or more target structures in the sample cell to the profile of the one or more target structures in the reference cell. In some embodiments, a difference in the profile of the sample cell as compared to the profile of the reference cell is indicative of an anomaly of the sample cell.

In some embodiments, the presently disclosed SERS-active nanoparticles can be used for staining microstructures within a cell. In such embodiments, the SERS-active nanoparticles can be labeled with at least one ligand that specifically binds to a known target microstructure or receptor. In some embodiments, a set of SERS-active nanoparticle probes can be used, wherein each member of the set comprises a combination of a ligand that specifically binds to a known target or receptor and one or more SERS-active dyes that can produce a distinguishable SERS signal upon binding with the target.

Under suitable conditions, the labeled SERS-active nanoparticles can specifically bind to receptors and other microstructures within the cell. The "stained" cells can then be imaged, for example, by using a scanning Raman microscope to determine the presence and location of specific receptors and microstructures in the cells. Further, the SERS signals from individual Raman-active dyes associated with a particular ligand can be used to distinguish between specific receptors and microstructures in the cell and to create a profile of the receptors and microstructures in the cell. The profile of a target cell assayed according to the presently disclosed method can be compared with a profile similarly obtained from a normal cell of the same type to determine the presence of an anomaly in the target cell. The target cell can be either living or dead.

As used herein, the term "microstructure" includes, but is not limited to, extracellular matrix molecules, such as fibronectin and laminin; intracellular structures, such as actin filaments and microtubes; cell nucleus structures, such as histone; and the like. Suitable ligands for binding to such microstructures can be selected from the ligands disclosed herein, and include, but are not limited to, antibodies, such as anti-fibronectin antibodies and anti-actin antibodies, and other naturally-occurring ligands, such as anti-histone protein.

Images of cells containing Raman spectral information can be obtained by a variety of methods known in the art. For example, a microscope can be coupled to a charge-coupled device (CCD) camera such that complete images of the sample can be obtained. Typically, in such embodiments, a wavenumber (or wavelength) filtering device, such as a monochromator or liquid crystal tunable filter, can be inserted between the sample and the CCD camera. The filtering device allows only a narrow bandwidth of scattered radiation to reach the CCD camera at any one time. Multiple images can be collected by the CCD camera, wherein each image covers a particular spectral range of the scattered radiation. The spectra from each point in the image can be assembled in software. Alternatively, light from a single point of an image can be dispersed through a monochromator and the complete spectrum of that point can be acquired on an array detector. The sample can be scanned such that each point in the image is acquired separately. The Raman image is then assembled in software. In another approach, a line scan instrument can be constructed that excites the sample with a line of radiation. The line is imaged spatially along one axis of a CCD camera while simultaneously being spectrally dispersed along the orthogonal axis. Each readout of the camera acquires the complete spectrum of each spatial pixel in the line. To complete the image the line is scanned across the sample. An example of a Raman instrument suitable for imaging is described in Talley, et al., "Nanoparticle Based Surface-Enhanced Raman Spectroscopy," NATO Advanced Study Institute: Biophotonics, Ottawa, Canada (Jan. 6, 2005).

In some embodiments, the presently disclosed SERS-active nanoparticles can be incorporated into a cell or tissue by a passive uptake mechanism. Another mechanism for incorporating nanoparticles into cells is through the use of small peptide, which can bind to endocytotic receptors on the cell surface and draw the nanoparticles into the cell through endocytosis. See Tkachenko, A. G., et al., "Cellular trajectories of peptide-modified gold particle complexes: comparison of nuclear localization signals and peptide transduction domains," *Bioconjugate Chem.*, 15, 482-490 (2004). Further, the SERS-active nanoparticles can be introduced into cells via microinjection, transfection, electroporation, and endocytosis-mediated approaches, including the use of amphipathic peptides, such as PEP-1, the use of cationic lipid-based reagents, such as LIPOFECTAMINE™ (Invitrogen Corp., Carlsbad, Calif., United States of America), and the use of micelles and transfection reagents such as transferrin, mannose, galactose, and Arg-Gly-Asp (RGD), and other reagents such as the dendrimer-based reagent SUPERFECT™ (Qiagen, Inc., Valencia, Calif., United States of America). Intracellularly, indirect methods can be used to show that the particles are bound to the desired targets. One method suitable for demonstrating the specificity of the probes is immunofluorescence, which can be used to verify the location of the SERS-active nanoparticles. A number of commercially available fluorescent probes are useful for labeling cellular structures (such as the mitochondria, Golgi apparatus and endoplasmic reticulum) in living cells. By conjugating an antibody that targets the same structure, the fraction of nanoparticles that actively label their target can be determined. Likewise, what percentage of nanoparticles that are non-specifically bound also can be determined. Another approach to verifying the location of the SERS-active nanoparticles is to use fluorescent protein fusions, such as GFP and its analogs.

In some embodiments, imaging agents comprising the presently disclosed SERS-active nanoparticles are provided for use in medical diagnosis. The presently disclosed imaging agents are useful in imaging a patient generally, and/or specifically diagnosing the presence of diseased tissue in a patient. As described hereinabove, by selecting the size, shape, and composition of the nanoparticle core; the identity of the dye; and the composition and thickness of encapsulant, if desired, the optimum excitation and emission frequencies of the SERS-active nanoparticles can be tuned to occur between about 630 nm and about 1000 nm, i.e., the minimum region for absorption and scattering by tissues.

An imaging process can be carried out by administering an imaging agent comprising one or more presently disclosed SERS-active nanoparticles to a cell, a tissue sample, or to a subject, such as a patient, and then scanning the cell, tissue sample, or subject using any system known in the art that can perform spectral imaging, including, but not limited to spot scanning confocal microscopes, line scanning systems, and Optical Coherence tomographic systems. The presence of the presently disclosed SERS-active nanoparticle in a cell, tissue sample, or subject also can be observed by any imaging systems that detects over a single wavelength band, as well as any fluorescence imaging system that includes an excitation light source and filtered image detection. Other imaging systems suitable for use with the presently disclosed SERS-active nanoparticles are described in Tuchin, V. V., *Handbook of optical biomedical diagnostics*, Bellingham, Wash., USA: SPIE Press, 2002, which is included herein by reference in its entirety. Other imaging methods, including time domain methods, such as dynamic light scattering spectroscopy and tomography, time-of-flight imaging, quasi-elastic light scattering spectroscopy, photon-correlation spectroscopy, Doppler spectroscopy, and diffusion wave spectroscopy are suitable for use with the presently disclosed subject matter. All these techniques allow differentiation between photons and where they have been based on their time signatures. Because SERS-active nanoparticles can have different time signatures than fluorescent substances and the like, they can be discriminated against tissues and other labels with these methods. Useful instrument parameters also include a modulated light source and time sensitive detector. The modulation can be pulsed or continuous.

The scanning of the cell, tissue sample, or subject provides spectra or images of an internal region of the cell, tissue sample, or subject and can be used to detect or diagnose the presence of a condition or a disease state. By region of a cell, tissue sample, or subject, it is meant the whole cell, tissue sample, or subject, or a particular area or portion of the cell, tissue sample, or subject. When the subject is a patient, the presently disclosed imaging agents can be used to provide images of internal organs of the patient, including vasculature, heart, liver, and spleen, and in imaging the gastrointestinal region or other body cavities, or in other ways as will be readily apparent to those skilled in the art, such as in tissue characterization, blood pool imaging, and the like.

The presently disclosed subject matter also provides, in some embodiments, a method of diagnosing abnormal pathology in vivo, the method including introducing a plurality of SERS-active nanoparticles targeted to a molecule involved in the abnormal pathology into a bodily fluid contacting the abnormal pathology, wherein the SERS-active nanoparticles can become associated with the molecule involved in the abnormal pathology, and imaging the associated SERS-active nanoparticles in vivo. The presently disclosed method is generally applicable to any organ accessible by the SERS-active nanoparticle probes, including the gastrointestinal tract, heart, lung, liver cervix, breast, and the like.

In some embodiments, the presently disclosed SERS-active nanoparticles can be introduced into a subject via an endoscope, as in the case of a colonoscopy, or a needle, or used with a disposable tip or sleeve, or via endocytosis, transfection, microinjection, and the like. In other embodiments, the SERS-active nanoparticle probes can be introduced by directly introducing the imaging probe itself. In some embodiments, individual optical fibers, or bundles of optical fibers, can be introduced into live organisms for imaging. Such methods have been demonstrated for imaging of nerves, brain, microvessels, cells, as well as for characterizing biodistribution. Gel-coated optical fibers are well known in the sensor literature. The presently disclosed SERS-active nanoparticles can be non-covalently bound to the gel, wherein the nanoparticles can diffuse into the tissue upon introduction into the tissue. A variety of other methods to immobilize SERS-active nanoparticles on the outer surface of fibers such that they can diffuse into liquid phases to which they are contacted also are suitable for use with the presently disclosed subject matter.

In some embodiments, the presently disclosed subject matter provides a method for labeling an animal with a SERS-active nanoparticle, the method comprising introducing a SERS-active nanoparticle into the animal. The presently disclosed SERS-active nanoparticles can be introduced into an animal by any suitable method, including, but not limited to, any subcutaneous implantation method or intravenously. The SERS-active nanoparticle can be detected using appropriate instrumentation. In some embodiments, the presently disclosed subject matter provides an identification system for animals, including livestock and domesticated pets, wherein the SERS-active nanoparticle is implanted under the skin (or hide) of the animal to enable identification.

III. Chemical Definitions

While the following terms are believed to be well understood by one of ordinary skill in the art, the following definitions are set forth to facilitate explanation of the presently disclosed subject matter. Unless otherwise defined, all technical and scientific terms used herein have the same meaning as commonly understood by one of ordinary skill in the art to which this presently described subject matter belongs.

Throughout the specification and claims, a given chemical formula or name shall encompass all optical and stereoisomers, as well as racemic mixtures where such isomers and mixtures exist.

When the term "independently selected" is used, the substituents being referred to (e.g., R groups, such as groups $R_1$, $R_2$, and the like, or groups $X_1$ and $X_2$), can be identical or different. For example, both $R_1$ and $R_2$ can be substituted alkyls, or $R_1$ can be hydrogen and $R_2$ can be a substituted alkyl, and the like.

A named "R" or "X" group will generally have the structure that is recognized in the art as corresponding to a group having that name, unless specified otherwise herein. For the purposes of illustration, certain representative "R" and "X" groups as set forth above are defined below. These definitions are intended to supplement and illustrate, not preclude, the definitions that would be apparent to one of ordinary skill in the art upon review of the present disclosure.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and alkenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, such as a 3- to 7-member substituted or unsubstituted cycloalkyl ring system, including one or more heteroatoms, which can be the same or different, and are selected from the group consisting of N, O, and S, and optionally can include one or more double bonds. The cycloheteroalkyl ring can be optionally fused to or otherwise attached to other cycloheteroalkyl rings and/or non-aromatic hydrocarbon rings. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The term "alkenyl" as used herein refers to a straight or branched hydrocarbon of a designed number of carbon atoms containing at least one carbon-carbon double bond. Examples of "alkenyl" include vinyl, allyl, 2-methyl-3-heptene, and the like.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a straight or branched hydrocarbon of a designed number of carbon atoms containing at least one carbon-carbon triple bond. Examples of "alkynyl" include propargyl, propyne, and 3-hexyne.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "heteroaryl" refers to an aromatic ring system, such as, but not limited to a 5- or 6-member ring system, including one or more heteroatoms, which can be the same or different, and are selected from the group consisting of N, O, and S. The heteroaryl ring can be fused or otherwise attached to one or more heteroaryl rings, aromatic or non-aromatic hydrocarbon rings, or heterocycloalkyl rings. Representative heteroaryl ring systems include, but are not limited to, pyridyl, pyrimidyl, pyrrolyl, pyrazolyl, azolyl, oxazolyl, isoxazolyl, oxadiazolyl, thiazolyl, isothiazolyl, imidazolyl, furanyl, thienyl, quinolinyl, isoquinolinyl, indolinyl, indolyl, benzothienyl, benzothiazolyl, enzofuranyl, benzimidazolyl, benzisoxazolyl, benzopyrazolyl, triazolyl, tetrazolyl, and the like.

A structure represented generally by the formula, wherein the ring structure can be aromatic or non-aromatic:

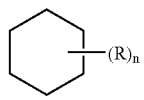

as used herein refers to a ring structure, for example, but not limited to a 3-carbon, a 4-carbon, a 5-carbon, a 6-carbon, and the like, aliphatic and/or aromatic cyclic compound, including a saturated ring structure, a partially saturated ring structure, and an unsaturated ring structure as defined herein, comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure above where n is 0 to 2 would comprise compound groups including, but not limited to:

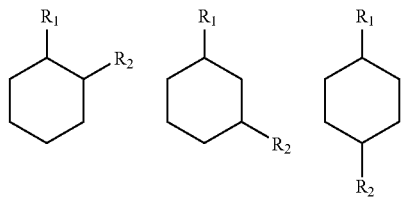

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

When a named atom of an aromatic ring or a heterocyclic aromatic ring is defined as being "absent," the named atom is replaced by a direct bond.

As used herein, the term "acyl" refers to an organic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Alkoxyl" refers to an alkyl-O— group wherein alkyl is as previously described. The term "alkoxyl" as used herein can refer to C$_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

The term "alkyl-thio-alkyl" as used herein refers to an alkyl-S-alkyl thioether, for example, a methylthiomethyl or a methylthioethyl group.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl. "Aralkoxycarbonyl" refers to an aralkyl-O—CO— group. An exemplary aralkoxycarbonyl group is benzyloxycarbonyl.

"Carbamoyl" refers to an $H_2N$—CO— group. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

The term "alkylamino" refers to an —NHR group wherein R is an alkyl group and/or a substituted alkyl group as previously described. Exemplary alkylamino groups include methylamino, ethylamino, and the like.

"Dialkylamino" refers to an —NRR' group wherein each of R and R' is independently an alkyl group and/or a substituted alkyl group as previously described. Exemplary dialkylamino groups include ethylmethylamino, dimethylamino, and diethylamino.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom. For example, a "thiol" group refers to the group —SH.

The term "sulfate" refers to the —$SO_4$ group.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Preparation of Nanoparticles Having Near-Infrared Dyes Attached Thereto

Spherical gold nanoparticles with a diameter of 60 nm were purchased from Ted Pella, Inc. (Redding, Calif., United States of America). The size of the nanoparticle as reported by the manufacturer was confirmed by transmission electron microscopy and light scattering. To attach Raman active species, e.g., non-fluorescent molecules and the presently disclosed NIR dyes, to the gold nanoparticles, the chemicals were mixed with gold nanoparticles such that the concentration of the Raman reporter was 10 µM in the final mixture. The gold nanoparticles were concentrated five times from their bulk solution to provide a final optical density equal to five (5) at 520 nm. The reaction was allowed to proceed overnight on a shaker.

Example 2

SERS Spectra of Near-Infrared Dyes

Figure 1:
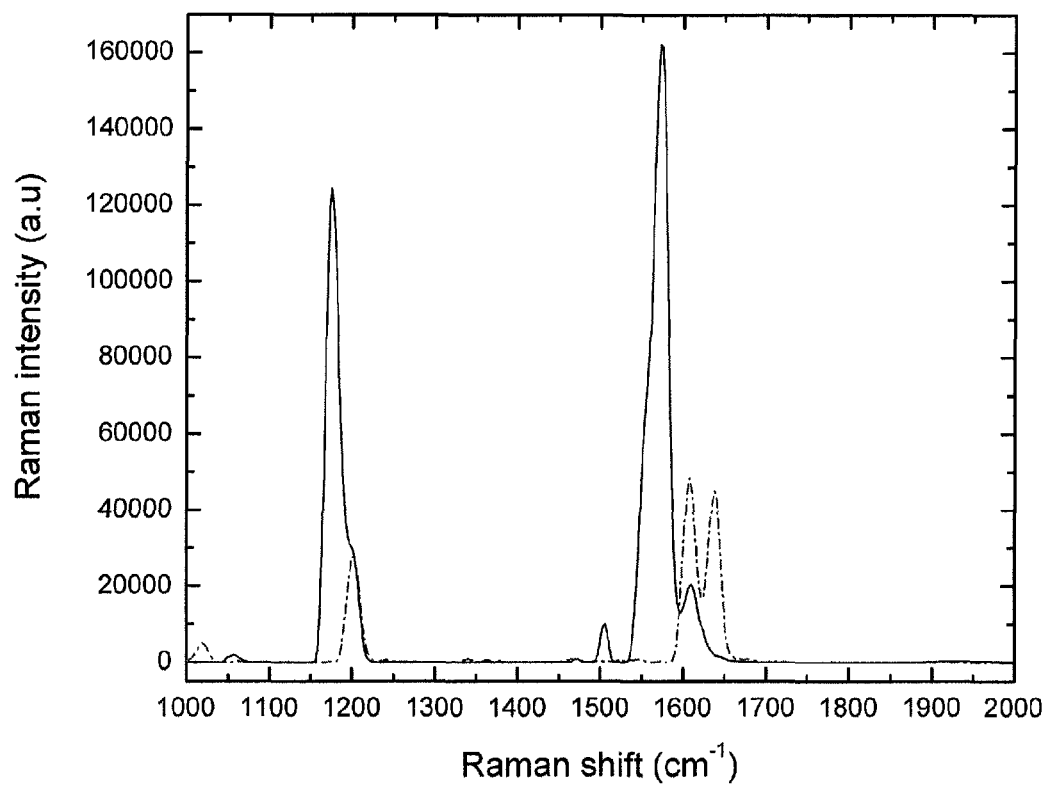

The instrument used for testing the SERS intensity of the presently disclosed SERS-active dyes was a Centice (Morrisville, N.C., United State of America) spectrometer with 660 nm laser excitation. The results of the experiments for a commonly-used non-fluorescent Raman active molecule, e.g., trans-1,2-bis(4-pyridyl)ethylene (BPE) and a presently disclosed NIR dye, e.g., Coumarin picolinium dye (CoPic) appear in FIG. 1. BPE exhibits two major peaks: one peak at approximately 1200 $cm^{-1}$ and a doublet between 1600 and 1650 $cm^{-1}$. Similarly, CoPic exhibits two major peaks at approximately 1150 and 1550 $cm^{-1}$. While the maximum intensity of the most prominent peak in the BPE spectrum is about 47,000, the maximum for CoPic is about 160,000. In this example, the peak maximum for CoPic is approximately three times as intense as that from BPE.

Figure 2:
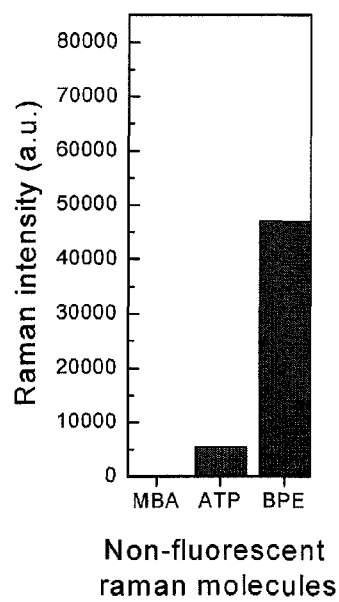
Figure 2:
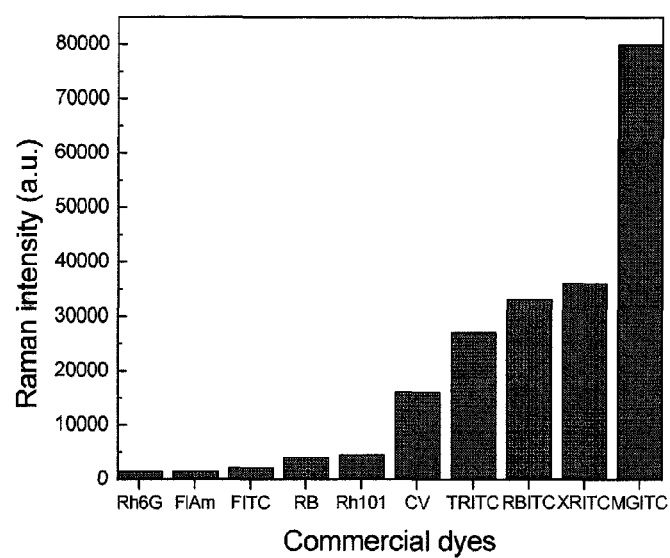
Figure 3:
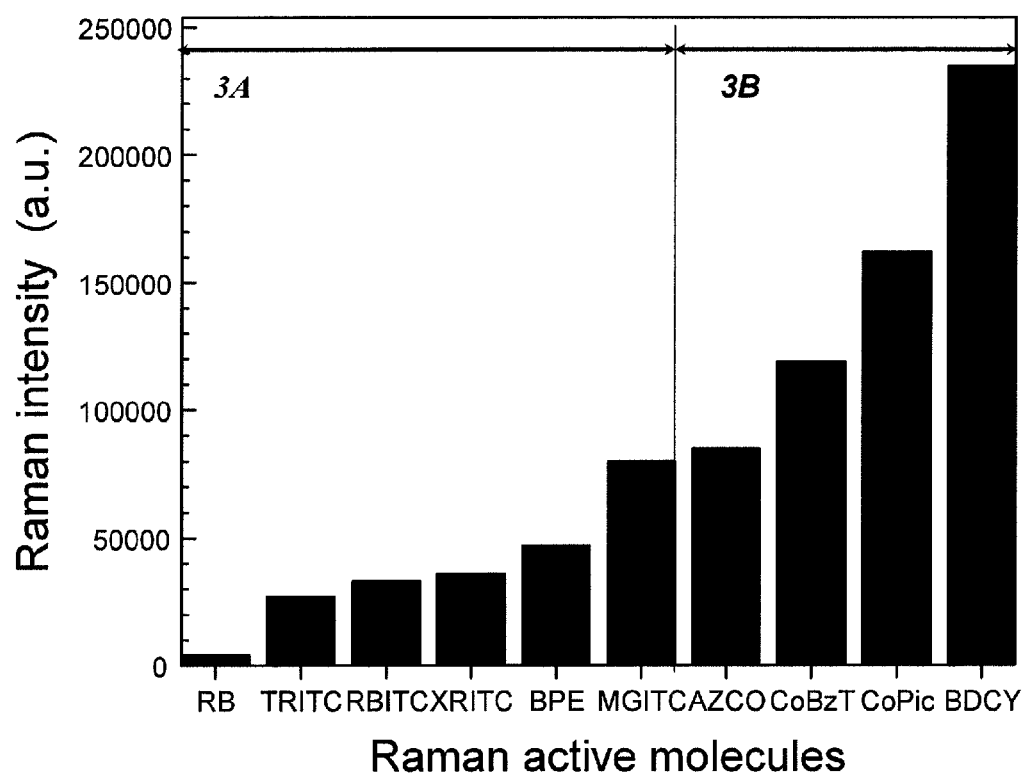
FIGS. 3A and 3B show a comparison of the Raman intensity of commercial Raman reporter molecules and commercial dyes (FIG. 3A) and the presently disclosed near-infrared dyes (FIG. 3B) adsorbed on spherical gold nanoparticles.
Figure 4:
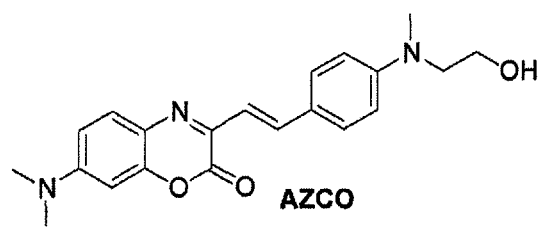
FIG. 4 shows chemical structures of representative embodiments of the presently disclosed near-infrared dyes.
Figure 4:
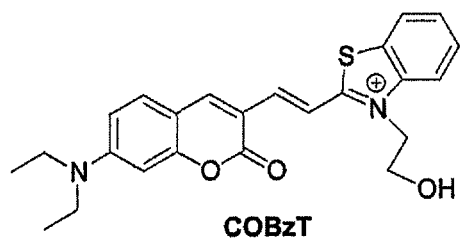
Figure 4:
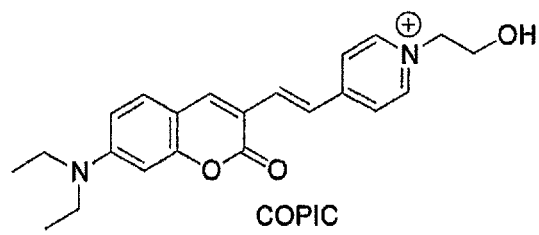
Figure 4:
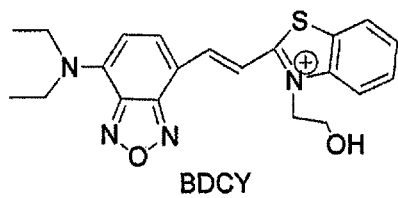

SERS data obtained for a number of commercially available non-fluorescent Raman molecules and dyes are presented in FIG. 2 and Table 1. In each case, the intensity of the most prominent Raman peak above the background is reported. All of the commercial dyes, except MGITC, do not perform as well as BPE. The intensity of the Raman peaks shown by the presently disclosed NIR dyes determined under similar experimental conditions is shown in FIG. 3. The structures of the dyes appear in FIG. 4. Some dyes did not show any Raman peaks, whereas other dyes exhibited intense peaks. FIG. 3 also compares the Raman intensity obtained for some commercially available Raman reporter molecules and the presently disclosed NIR dyes. In some embodiments, the presently disclosed dyes are two to five times more intense that reporter molecules known in the art at 660 nm laser excitation.

TABLE 1

Raman Intensity Observed at Most Intense Peak for Representative Commercially-Available Raman Molecules and Dyes.

| No. | Abbreviation | Name | Source | Intensity Arbitrary Units (a.u.) | Primary Peak (cm$^{-1}$) |
|---|---|---|---|---|---|
| 1 | MBA | 4-mercaptobenzoic acid | Sigma† | 100 | 1590 |
| 2 | ATP | 4-aminothiophenol | Sigma† | 5500 | 1528 |
| 3 | BPE | Trans-1,2-bis(4-pyridyl)ethylene | Sigma† | 47000 | 1608 |
| 4 | Cy-5 | Cyanine-5 | Amersham‡ | 100 | — |
| 5 | Rh6G | Rhodamine6G | Sigma† | 1500 | 1457 |
| 6 | FlAm | Fluorescamine | Sigma† | 1500 | 1599 |
| 7 | FITC | Fluorescein isothiocyanate | Sigma† | 2000 | 1599 |
| 8 | RB | RhodamineB | Sigma† | 4000 | 1515 |
| 9 | Rh101 | Rhodamine 101 | Sigma† | 4500 | — |
| 10 | CV | Cresyl violet | Sigma† | 16000 | 1638 |
| 11 | TRITC | Tetramethyl-rhodamine isothiocyanate | Sigma† | 27000 | 1651 |
| 12 | RBITC | RhodamineB isothiocyanate | Sigma† | 33000 | 1515 |
| 13 | XRITC | X-rhodamine-5-(and -6)isthiocyanate | Molecular Probes ®†† | 36000 | 1648 |
| 14 | MGITC | Malachite green isothiocyanate | Molecular Probes ®†† | 80000 | 1623 |

†Sigma-Aldrich Co., St. Louis, Missouri;
‡Amersham Biosciences, Piscataway, New Jersey;
††Invitrogen Corporation, Carlsbad, California.

TABLE 2

Raman Intensity Observed at Most Intense Peak for Representative Presently Disclosed Near-Infrared Raman Dyes.

| No. | Abbreviation | Name | Intensity (a.u.) | Primary Peak (cm$^{-1}$) |
|---|---|---|---|---|
| 15 | ERB | Eno Red B | 100 | — |
| 18 | AZCO | Iodoacetyl aza-coumarin | 85000 | 1650 |
| 19 | CoBzt | Coumarin benzothiazole | 119000 | 1560 |
| 20 | CoPic | Coumarin picolinium | 162000 | 1573 |
| 21 | BDCY | Benzodioxazole cyanine | 235000 | 1555 |

Example 3

Reduction of Non-Specific Binding in Magnetic Capture Liquid-Based SERS Assays

Figure 5:
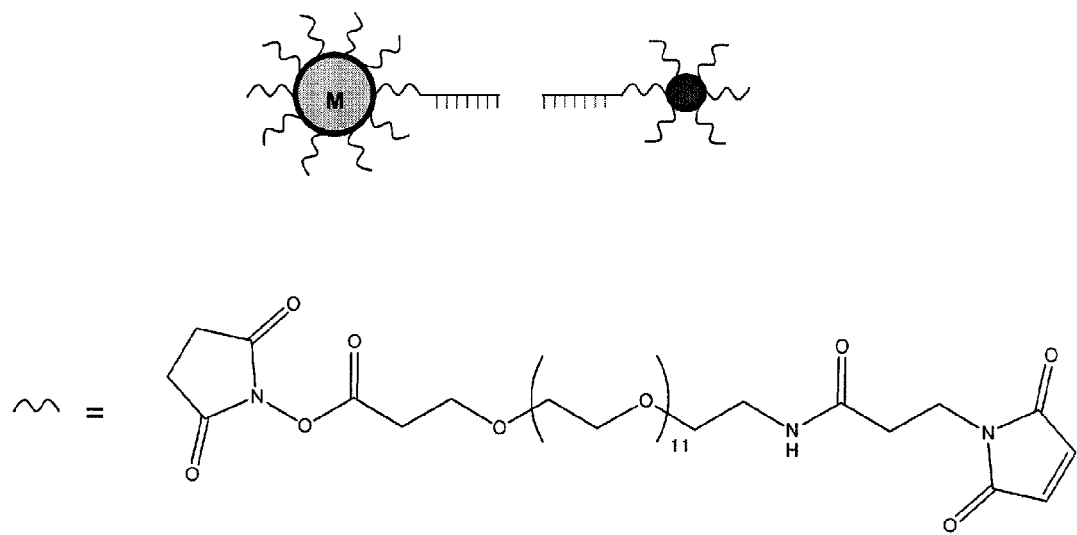
FIG. 5 is a schematic showing DNA probes immobilized to magnetic particle (M) and a SERS-active nanoparticle via a polyethylene glycol (PEG) linker according to one embodiment of the presently disclosed subject matter (only one probe shown for clarity and not drawn to scale)

DNA oligonucleotides were attached to the surface of SERS-active nanoparticles (gold particles coated with SERS-active reporter molecules, e.g., various bipyridyl dyes, and encapsulated by a thiol-functionalized glass coating) through a polyethylene glycol (PEG) linker molecule. A representative example of one embodiment of the presently disclosed subject matter is illustrated in FIG. 5, which depicts the immobilization of DNA on the surface of SERS-active nanoparticles and magnetic capture particles via a 5-nm heterobifunctional PEG linker molecule.

The amine-terminated oligonucleotides were reacted with the N-hydroxy-succinimide (NHS) ester moiety of a heterobifunctional polyethylene glycol molecule comprising an NHS ester separated from a thiol-reactive maleimide group by twelve ethylene glycol subunits. Immobilization of PEGylated DNA on SERS-active nanoparticles was accomplished by the reaction of maleimide groups on the PEG linker with thiol groups present on the surface of the SERS-active nanoparticle.

DNA oligonucleotides conjugated to a heterobifunctional PEG molecule were coupled to magnetic particles through traditional 1-ethyl-3-(3-dimethylaminopropyl)-carbodiimide (EDC) coupling by treating carboxylated magnetic particles with an amine-terminated molecule containing an internal disulfide. The disulfide was then cleaved with dithiothreitol, exposing a reactive thiol group that reacted with the maleimide moiety of the oligonucleotide-PEG conjugate.

To measure the non-specific binding between the oligonucleotide-coated SERS-active nanoparticle and the oligonucleotide-coated magnetic particle, 10 μL of a 1-mg/mL solution of oligonucleotide-coated magnetic particles were mixed with 100 μL of a 10-pM solution of oligonucleotide-coated SERS particles and 100 μL of buffer in a small tube. The tube was inverted for 30 to 120 minutes, followed by concentration of the magnetic particles with a magnet to form a pellet. The pellet was subsequently interrogated with a laser to determine the level of SERS signal, which is proportional to the number of SERS-active reporter molecules associated with the magnetic particles in the pellet.

FIG. 6A shows one spectrum of a blank sample tube and another of SERS-active nanoparticles and magnetic particles mixed together, wherein a DNA oligonucleotide has been directly attached (no PEG linker) to the SERS-active nanoparticle and the magnetic particle via a biotin-streptavidin strategy. Due to the lack of target DNA (analyte) in the solution, the observed SERS signal is due to non-specific association of the SERS-active nanoparticle with the magnetic particles. FIGS. 6B and 6C show results from a similar assay performed with oligonucleotide-coated SERS-active nanoparticles and oligonucleotide-coated magnetic particles, wherein the oligonucleotides are attached via a PEG linker and prepared as described above. FIGS. 6A and 6B are plotted on the same scale. FIG. 6C presents the same data as FIG. 6B, but over a narrower signal range. FIG. 6C highlights the similarity between the signal from the tube alone and the assay signal, demonstrating that non-specific binding between the two sets of particles has been nearly eliminated.

Although the foregoing subject matter has been described in some detail by way of illustration and example for purposes of clarity of understanding, it will be understood by those skilled in the art that certain changes and modifications can be practiced within the scope of the appended claims.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

That which is claimed:

1. A surface-enhanced Raman spectroscopy (SERS)-active nanoparticle having associated therewith at least one SERS-active reporter molecule of the formula:

A-Y wherein:
A is:

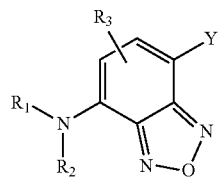

Y is:

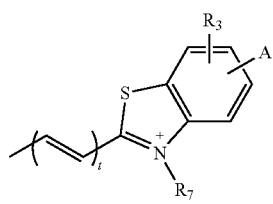

wherein:
r, s, and t are each independently an integer from 1 to 8;
wherein:
each $R_1$, $R_2$, $R_3$, $R_8$, $R_{10}$, $R_{11}$, is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoa;kyl, acyloxyl, alkylaminoalkyl, and alkoxycarbonyl; $R_7$ is Z';
wherein Z' is selected from the group consisting of:

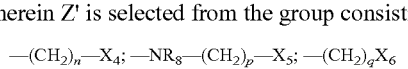

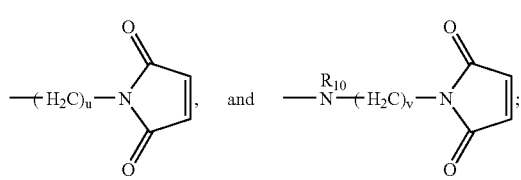

wherein:
n, p, q, u, and v are each independently an integer from 1 to 8;
$X_4$ and $X_5$ are each independently selected from the group consisting of hydroxyl, amino, and thiol;
$X_6$ is O or $NR_{11}$;
$R_9$ is —$(CH_2)_m$—$X_7$ or —$(CH_2)_m$—B, wherein
m is an integer from 1 to 8;
$X_7$ is halogen; and
B is a binding member having a binding affinity for a ligand or analyte to be detected.

2. The SERS-active nanoparticle of claim 1, wherein the SERS-active reporter molecule of formula A-Y is

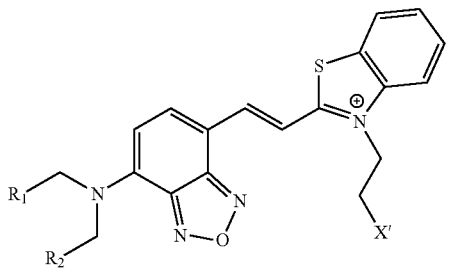

wherein:
X' is selected from the group consisting of hydroxyl, amino, and thiol; and each $R_1$ and $R_2$ is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxycycloalkyl, aminoalkyl, acyloxyl, alkylaminoalkyl, and alkoxycarbonyl.

3. The SERS-active nanoparticle of claim 1, wherein the SERS-active reporter molecule of formula A-Y is adsorbed on an outer surface of the nanoparticle.

4. The SERS-active nanoparticle of claim 1, wherein the SERS-active reporter molecule of formula A-Y is covalently bound to an outer surface of the nanoparticle.

5. The SERS-active nanoparticle of claim 1, wherein the nanoparticle comprises a metal selected from the group consisting of Au, Ag, Cu, Na, Al, and Cr.

6. The SERS-active nanoparticle of claim 1, wherein the nanoparticle comprises an alloy of at least two metals selected from the group consisting of Au, Ag, Cu, Na, Al, and Cr.

7. The SERS-active nanoparticle of claim 1, wherein the nanoparticle has a diameter less than about 200 nm.

8. The SERS-active nanoparticle of claim 1, wherein the nanoparticle has a diameter between about 40 nm to about 100 nm.

9. The SERS-active nanoparticle of claim 1, wherein the SERS-active reporter molecule of formula A-Y forms a layer on an outer surface of the nanoparticle, wherein the layer at least partially covers the outer surface of the nanoparticle and is defined by an inner surface and an outer surface.

10. The SERS-active nanoparticle of claim 9, wherein the layer of the SERS-active reporter molecule of formula A-Y formed on the outer surface of the nanoparticle is selected from the group consisting of a submonolayer, a monolayer, and a multilayer.

11. The SERS-active nanoparticle of claim 10, further comprising an encapsulant, wherein the encapsulant is disposed on at least one of the outer surface of the nanoparticle and the outer surface of the layer of the SERS-active reporter molecule of formula A-Y.

12. The SERS-active nanoparticle of claim 11, wherein the encapsulant comprises one or more materials selected from the group consisting of a glass, a polymer, a metal, a metal oxide, and a metal sulfide.

13. The SERS-active nanoparticle of claim 12, wherein the glass comprises $SiO_x$.

14. The SERS-active nanoparticle of claim 12 wherein the encapsulant has a thickness of about 1 nm to about 40 nm.

15. A kit comprising a reagent comprising one or more surface-enhanced Raman spectroscopy (SERS)-active nanoparticles having associated therewith at least one SERS-active reporter molecule of Formula:

A-Y wherein:
A is:

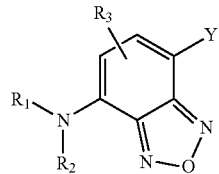

Y is:

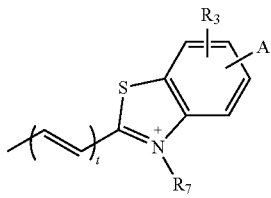

wherein:
r, s, and t are each independently an integer from 1 to 8;
wherein:
each $R_1, R_2, R_3, R_8, R_{10}, R_{11}$, is independently selected from the group consisting of H, alkyl, substituted alkyl, heteroalkyl, substituted heteroalkyl, cycloalkyl, substituted cycloalkyl, cycloheteroalkyl, substituted cycloheteroalkyl, aryl, substituted aryl, aralkyl, hydroxyl, alkoxyl, hydroxyalkyl, hydroxycycloalkyl, alkoxcycloalkyl, aminoalkyl, acyloxyl, alkylaminoalkyl, and alkoxycarbonyl; $R_7$ is Z';

wherein Z' is selected from the group consisting of:

—$(CH_2)_n$—$X_4$; —$NR_8$—$(CH_2)_p$—$X_5$; —$(CH_2)_q X_6$ C(=O)—$R_9$,

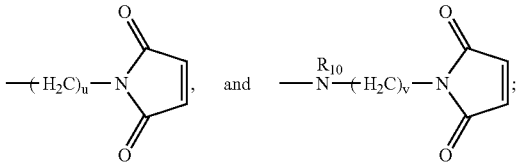

wherein:
n, p, q, u, and v are each independently an integer from 1 to 8;
$X_4$ and $X_5$ are each independently selected from the group consisting of hydroxyl, amino, and thiol;
$X_6$ is O or $NR_{11}$;
$R_9$ is —$(CH_2)_m$—$X_7$ or —$(CH_2)_m$—B, wherein
m is an integer from 1 to 8;
$X_7$ is halogen; and
B is a binding member having a binding affinity for a ligand or analyte to be detected.

16. The kit of claim 15, further comprising one or more of a sample collection device, magnetic capture particles, a buffer solution, and combinations thereof.

17. The kit of claim 16, wherein the reagent is disposed in the sample collection device.

18. The kit of claim 15, wherein the one or more surface-enhanced Raman spectroscopy (SERS)-active nanoparticles comprise a plurality of SERS-active nanoparticles, each having associated therewith a SERS-active reporter molecule having a distinguishable SERS response, and wherein at least one of the SERS-active reporter molecules comprises a SERS-active reporter molecule of Formula A-Y.

* * * * *

UNITED STATES PATENT AND TRADEMARK OFFICE
CERTIFICATE OF CORRECTION

| | |
|---|---|
| PATENT NO. | : 8,962,342 B2 |
| APPLICATION NO. | : 12/134594 |
| DATED | : February 24, 2015 |
| INVENTOR(S) | : Joseph Thomas et al. |

It is certified that error appears in the above-identified patent and that said Letters Patent is hereby corrected as shown below:

In the claims
Column 55, line 40, Claim 1, "aminoa;kyl" should read -- aminoalkyl --.

Signed and Sealed this
Seventeenth Day of November, 2015

Michelle K. Lee
*Director of the United States Patent and Trademark Office*